(12) United States Patent
Ott

(10) Patent No.: US 7,678,833 B2
(45) Date of Patent: Mar. 16, 2010

(54) METHOD TO INCREASE THE BIOAVAILABILITY OF CYSTEINE

(75) Inventor: David M. Ott, Oakland, CA (US)

(73) Assignee: Allium Vitalis Incorporated, Berkeley, CA (US)

( * ) Notice: Subject to any disclaimer, the term of this patent is extended or adjusted under 35 U.S.C. 154(b) by 140 days.

(21) Appl. No.: 11/805,637

(22) Filed: May 23, 2007

(65) Prior Publication Data

US 2007/0275876 A1  Nov. 29, 2007

Related U.S. Application Data

(60) Provisional application No. 60/808,329, filed on May 24, 2006.

(51) Int. Cl.
  *A23L 1/30* (2006.01)
  *A61K 31/10* (2006.01)
  *A61K 38/02* (2006.01)
(52) U.S. Cl. .............. 514/706; 424/439; 426/547; 426/648; 514/2; 514/707
(58) Field of Classification Search .................. None
  See application file for complete search history.

(56) References Cited

U.S. PATENT DOCUMENTS

2001/0053356 A1* 12/2001 Mousa ................. 424/94.1
2004/0235946 A1* 11/2004 Ott ........................ 514/517

FOREIGN PATENT DOCUMENTS

EP           0 653 206 A1 *    5/1995

OTHER PUBLICATIONS

Yao et al., Protective effect of glucose-cysteine adduct on in situ perfused liver; Amino Acids 12:33, (1997).
Droge, Oxidative Stress and Aging; Advances in Experimental and Medical Biology 543:191, Kluwer Academic/Plenum Publishers, New York, 2003.
Droge et al., Modulation of Lymphocyte Functions and Immune Response by Cysteine and Cysteine Derivatives; The American Journal of Medicine 91:3C-140S, (1991).
Buono et al., Total Sulfur Amino Acid Requirement in Young Men as Determined by Indicator Amino Acid Oxidation; American Journal of Clinical Nutrition 74:756, (2001).
Cantin et al., Albumin-mediated Regulation of Cellular Glutathione and Nuclear Factor Kappa B Activation; American Journal of Respiratory and Critical Care Medicine 162:1539, (2001).

(Continued)

*Primary Examiner*—Jeffrey E Russel

(57) ABSTRACT

A method for increasing the bioavailability of cysteine within an animal by reducing extracellular cysteine disulfide molecules to produce extracellular cysteine molecules. A membrane permeable thiol molecule that forms a membrane permeable disulfide molecule after becoming oxidized participates in thiol-disulfide exchange reactions on both sides of the cellular membrane, crossing the membrane randomly via simple diffusion. The membrane permeable disulfide, within or upon entering the highly reductive environment of a cell, becomes reduced to form a membrane permeable thiol molecule. the membrane permeable thiol can then diffuse to the exterior of the cell, where it is available to reduce another cystine molecule. This process can continue cycling, producing net cumulative increase in the concentration of extracellular cysteine. This is beneficial for providing cysteine as a nutrient to cells that require cysteine for nourishment.

19 Claims, 4 Drawing Sheets

OTHER PUBLICATIONS

Taurine; Alternative Medicine Review 6:78, (2001).

Mansoor et al., Determination of the in vivo redox status of cysteine, cysteinylglycine, homocysteine, and glutathione in human plasma; Analytical Biochemistry 200:218, (1992).

Post et al., "The effect of aging on constitutive mRNA levels . . ." in "Physiological Senescence and its Postponement", The New York Academy of Sciences, New York 1991.

Rahbar, "The discovery of glycated hemoglobin" in "The Maillard Reaction", The New York Academy of Sciences, New York, 2005.

Szwergold et al., "Transglycation—a potential new mechanism for deglycation of Schiff's bases" in "The Maillard Reaction", The New York Academy of Sciences, New York, 2005.

Khan et al., Magnitude of Arsenic Toxicity in Tube-well Drinking Water in Bangladesh and Its Adverse Effects on Human Health . . . ; Asian Pacific Journal of Cancer Prevention 4:7, (2003).

Greipp, Hyperpigmentation Syndromes (Diffuse Hypermelanosis); Archives of Internal Medicine 138:356, (1978).

Meister et al., Glutathione; Annual Review of Biochemistry 52:711, (1988).

Droge, The Plasma Redox State and Ageing; Ageing Research Reviews 1:257, (2002).

Chen et al., Atherogenicity and Carcinogenicity of High-Arsenic Artesian Well Water; Arterisclerosis 8:452, (1998).

Ochi, Arsenic compound-induced increases in glutathione levels in cultured Chinese hamster V79 cells and mechanisms associated with changes . . . ; Archives of Toxicology 71:730, (1997).

Hayakawa et al; A new metabolic pathway of arsenite: arsenic-glutathione complexes are substrates for human arsenic methyltransferase Cyt19; Archives of Toxicology 79:183, (2005).

Bremer et al., Enzymic Methylation of Foreign Sulfhydryl Compounds; Biochimica et Biophysica Acta 46:217, (1961).

Piscioto et al., Induction of Mucosal Glutathione Synthesis by Arsenic; Biochemica et Biophysica Acta 628:241, (1980).

Cotgreave et al., Recent Trends in Glutathione Biochemistry—Glutathione-Protein Interactions . . . ; Biochemical and Biophysical Research Communications 242:1, (1998).

Wills, Enzyme Inhibition by Allicin, the Active Principle of Garlic; Biochemical Journal 63:514, (1956).

Crawhall et al., The intracellular Ratio of Cysteine to Cystine in Various Tissues; Biochemical Journal 105:891, (1967).

Hack et al., The redox state as a correlate of senescence and wasting and as a target for therapeutic intervention; Blood 92:59, (1998).

Dai et al., Malignant Cells Can Be Sensitized to Undergo Growth Inhibition and Apoptosis by Arsenic Trioxide Through Modulation of the Glutathione Redox System; Blood 93:268, (1999).

Sondet et al., Mitochondria-targeting drugs arsenic trioxide and Ionidamine bypass the resistance of TPA-differentiated leukemic cells to apoptosis; Blood 97:3931, (2001).

Grad et al., Ascorbic acid enhances arsenic trioxide-induced cytotoxicity in multiple myeloma cells; Blood 98:805, (2001).

Gyamlani et al., Acetaminophen toxicity: suicidal vs accidental; BioMed. Central Critical Care 6:155, (2002).

Chasseaud, Reaction with electrophiles after enzyme-catalysed deacetylation of N-acetylcysteine; Biochemical Pharmacology 23:1133, (1974).

Das et al., Nitric Oxide Synthase is a Unique Mechanism of Garlic Action; Biochemical Society Transactions 23:S136, (1995).

Smith et al., Contamination of drinking-water by arsenic in Bangladesh: a public health emergency; Bulletin of the World Health Organization 78:1093, (2000).

Neuhouser et al., Fruits and Vegetables Are Associated with Lower Lung Cancer Risk Only in the Placebo Arm . . . ; Cancer Epidemiology, Biomarkers & Prevention 12:350, (2003).

Birwe et al., High-performance liquid chromatographic determination of urinary cysteine and cystine; Clinica Chimica Acta 67:417, (1991).

Mortensen et al., Glucosylation of human haemoglobin A. Dynamic variation in HbA1c described by a biokinetic model; Clinica Chimica Acta 136:75, (1984).

Herrmann et al., Disturbed Homocysteine and Methionine Cycle Intermediates S-Adenosylhomocysteine and S-Adenosylmethionine Are Related . . . ; Clinical Chemistry 51:5, (2005).

Hu et al., Arsenic trioxide induces apoptosis in cells of MOLT-4 and its daunorubicin-resistant cell line via depletion of . . . ; Cancer Chemotherapy and Pharmacology 52:47, (2003).

Bahlis et al., Feasibility and Correltaes of Arsenic Trioxide Combined with Ascorbic Acid-mediated Depletion of Intrecellular Glutathone . . . ; Clinical Cancer Research 8:3658, (2002).

Sparnins et al., Effects of organosulfur compounds from garlic and onions on benzo[a] pyrene-induced neoplasia and glutathione S-transferase activity . . . ; Carcinogenesis 9:131, (1988).

Droge., Cysteine and glutathione in catabolic conditions and immunological dysfunction; Current Opinion in Clinical Nutrition and Metabolic Care 2:227, (1999).

Shirin et al., Antiproliferative Effects of S-Allylmercaptocysteine on Colon Cancer Cells When Tested Alone or in Combination with Sulindac Sulfide; Cancer Research 61:725, (2001).

Scott et al., Reactions of Arsenid (III) and Arsenic (V) Species with Glutathione; Chemical Research in Toxicology 6:102, (1993).

Styblo et al., Comparative Inhibition of Yeast Glutathione Reductase by Arsenicals and Arsenothiols; Chemical Research in Toxicology 10:27, (1997).

Droge., Aging-related changes in the thiol/disulfide redox state: implications for the use of thiol antioxidants; Experimental Gerontology 37:1331, (2002).

Smith et al., Arseinc-Induced Skin Leaions among Atacameno People in Northern Chile Despite Good Nutrition and Centuries of Exposure; Environmental Health Perspectives 108:617, (2000).

Mitra, et al., Nutritional Factors and Susceptibility to Arsenic Caused Skin Lesions in West Bengal, India; Environmental Health Perspectives 112:1104, (2001).

Jocelyn, The Standard Redox Potential of Cysteine-Cystine from the Thiol-Disulfide Exchange Reaction with Glutathione and Lipolic Acid; European Journal of Biochemistry 2:327, (1967).

De Rosa et al., N-acetylcysteine replenishes glutathione in HIV infection; European Journal of Clinical Investigation 30:915, (2000).

Beaver et al., A decrease in intracellular glutathione concentration precedes the onset of apoptosis in murine thymocytes; European Journal of Cell Biology 68:47, (1995).

Das et al., Modification of Clastogenicity of Three Known Clastogens by Garlic Extract in Mice in Vivo; Environmental and Molecular Mutagenesis 21:383, (1993).

Maiti et al., Differential response of cellular antioxidant mechanism of liver and kidney to arsenic exposure . . . ; Environmental Toxicology and Pharmacology 8:227 (2000).

Kawakami et al., Identification and characterization of oxidized human serum albumin; FEBS Journal 273:3346, (2006).

Mendiratta et al., Erythrocyte Ascorbate Recycling: Antioxidant Effects in Blood; Free Radicals in Biology and Medicine 24:789, (1998).

Shannon et al., Arsenic-induced Skin Toxicity; Human Toxicology 8:99, (1989).

Mazumder et al., Arsenic levels in drinking water and the prevalence of skin lesions in West Bengal, India; International Journal of Epidemiology 27:871, (1998).

Lawson et al., Allicin and Allicin-Derived Garlic Compounds Increase Breath Acetone through Allyl Methyl Sulfide . . . ; Journal of Agricultural and Food Chemistry 53:1974, (2005).

Zhang et al., Structural Requirements for the Binding of Modified Proteins to the Scavenger Receptor of Macrophages; The Journal of Biological Chemistry 268:5535, (1993).

Kala et al., The MRP2/cMOAT Transporter and Arsenic-Glutathione Complex Formation Are Required for Biliary Excretion of Arsenic; The Journal of Biological Chemistry 275:33404, (2000).

Bald et al., Analysis of plasma thiols by high-performance liquid chromatography with ultraviolet detection; Journal of Chromatography A 1032:109, (2004).

Yang et al., Effect of ageing on human plasma glutathione concentrations as determined by high-performance liquid . . . ; Journal of Chromatography B Biomedical Applications 674:2 (1995).

Orringer et al., An Ascorbate-Mediated Transmembrane-Reducing System of the Human Erythrocyte; Journal of Clinical Investigation 63:53, (1979).

Ishii et al., Regulation of Glutathione Levels in Mouse Spleen Lymphocytes by Transport of Cysteine; Journal of Cellular Physiology 133:330, (1987).

Mazumder, Chronic Arsenic Toxicity: Clinical Features, Epidemiology, and Treatment: Experience in West Bengal; Journal of Environmental Science and Health; A38:141, (2003).

Wierzbicka et al., Glutathione in Food; Journal of Food Composition and Analysis 2:327, (1989).

Villa et al., Glutathione protects mice from lethal sepsis by limiting inflammation and potentiating host defense; Journal of Infectious Diseases 185:1115, (2002).

Barnhart et al., Concentration-dependent antioxidant activity of probucol in low density lipoproteins in vitro . . . ; Journal of Lipid Research 30:1703, (1989).

Breitkreutz et al., Improvement of immune functions in HIV infection by sulfur supplementation: two randomized trials; Journal of Molecular Medicine 78:55, (2000.

Freidman et al., Nutritional Improvement of Soy Flour; Journal of Nutrition 114:2241, (1984).

Lau, Suppression of LDL Oxidation by Garlic; Journal of Nutrition 131, supplement 3S:985S, (2001).

Mariotti et al., Acute ingestion of dietary proteins improves post-exercise liver glutathione in rats in a dose-dependent relationship . . . ; Journal of Nutrition 134:128, (2004).

Blair et al., Oral L-2-Oxo-4-thiazolidine Reduces Bacterial Translocation after Radiation in the Fischer Rat; Journal of Surgical Research 65:165, (1996).

Hildebrandt et al., Plasma cystine concentration and redox state in aging and physical exercise; Mechanisms of Ageing and Development 123:1269, (2002).

Szwergold., alpha-Thiolamines such as cysteine and cysteamine act as effective transglycating agents due to formation of irreversible . . . ; Medical Hypotheses 66:698, (2006).

Liu et al., Overexpression of Glutathione S-Transferase II and Multidrug Resistance Transport Proteins Is Associated with Acquired Tolerance . . . ; Molecular Pharmacology 60:302, (2001).

Hamm et al., Changes in the Sulphydryl and Disulfide Groups in Beef Muscle Proteins During Heating; Nature 207:1269, (1965).

O'Mullan et al., Sniffing Out the Truth; The New York Times, Jan. 21, 2007.

Turin; What You Can't Smell Will Kill You; The New York Times, Jan. 21, 2007.

Nakagawa et al., Prevention of Liver Damage by Aged Garlic Extract and Its Components in Mice; Phytotherapy Research 3:50, (1989).

Jung et al., Effect of Different Garlic Preparations on the Fluidity of Blood, Fibrolytic activity, and Peripheral Microcirculation in comparison with . . . ; Planta Medica 56:668, (1990).

Lawson et al., Pre-Hepatic Fate of the Organosulfur Compounds Derived from Garlic (Allium sativum); Planta Medica 59:A688, (1993).

Liu et al., Induction of oxyradicals by arsenic: Implication for mechanism of genotoxicity; Proceedings of the National Academy of Seicnce 98:1643, (2001).

Droge, Oxidative stress and ageing: is ageing a cysteine deficiency syndrome? Philosophical Transactions of the Royal Society 360:2355, (2005).

Tateishi et al., "Regulation of Glutathione Level in . . . " in "Glutathione Centennial: Molecular Perspectives and Clinical Implications", Academic Press, New York, 1989.

Bannai et al., "Regulation of Glutathione Level by . . . " in "Glutathione Centennial: Molecular Perspectives and Clinical Implications", Academic Press, New York, 1989.

Barron et al., Enzyme Systems Containing Active Sulphydryl Groups. The Role of Glutathione; Science 97:356, (1943).

Zakharyan et al., Arsenite Methylation by Methylvitamin B12 and Glutahtione Does Not Require an Enzyme; Toxicology and Applied Pharmacology 154:287, (1999).

Brambila et al., Chronic Arsenic-Exposed Human Prostate Epithelial Cells Exhibit Stable Arsenic Tolerance . . . ; Toxicology and Applied Pharmacology 183:99, (2002).

Chen et al., Biomarkers of exposure, effect, and susceptibility of arsenic-induced health hazards in Taiwan; Toxicology and Applied Pharmacology 206:198, (2005).

Vahter et al., Effects of Low Dietary Intake of Methionine, Choline or Proteins on the Biotransformation of Arsenite in the Rabbit; Toxicology Letters 37:41, (1987).

White et al., Toxicity Evaluations of L-cysteine and Procysteine, a Cysteine Prodrug, Given Once Intravenously to Neonatal Rats; Toxicology Letters 69:15, (1993).

Huang et al., Glutathione as a cellular defence against arsenite toxicity in cultured Chinese hamster ovary cells; Toxicology 79:195, (1993).

Gomez et al. Attenuation of acetaminophen hepatotoxicity in mice as evidence for the bioavailability of the cysteine in D-glucose-L-cysteine in vivo; Toxicology Letters 70:101, (1994).

Schuliga et al., Upregulation of Glutathione-Related Genes and Enzyme Activities in Cultured Human Cells by Sublethal Concentrations of . . . ; Toxicological Sciences 70:183, (2002).

Kojima et al., Chronic Exposure to Methylated Arsenicals Stimulates Arsenic Excretion Pathways and Induces Arsenic Tolerance in Rat Liver Cells; Toxicological Sciences 91:70, (2006).

\* cited by examiner

METHOD TO INCREASE THE BIOAVAILABILITY OF CYSTEINE

This application claims the benefit of provisional application No. 60/808,329 filed May 24, 2006.

FIELD OF THE INVENTION

The present invention relates to methods for improving the bioavailability of the endogenous biothiols cysteine and glutathione, which are known to be beneficial and for the prevention and treatment of cysteine depletion dependant diseases. The present invention provides a method of treating a cysteine depletion dependant disease or condition and for maintaining good health in an animal. Examples of use include the treatment of diseases such as arsenicosis, diabetes and AIDS.

BACKGROUND OF THE INVENTION

1. DEFINITIONS, GLOSSARY, AND ABBREVIATIONS

Activate, activation: To initiate or increase the activity, e.g. to increase the activity of an enzyme.

Administration of a compound: Causing a compound to enter into the body of an animal, either orally, by injection, or by any other means.

Allyl mercaptan; AllylSH: chemical name AllylThiol; chemical formula:

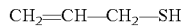

In the present exposition allyl mercaptan is the model thiol compound. In general, a compound is referred to herein as a "model" compound when it is representative of a more general class of compounds defined herein.

AllylMercapto radical; AllylS*: allyl mercaptan without the terminal hydrogen atom of the SH group, resulting in an unpaired electron on the sulfur atom which is available for covalent bonding to the remainder of a larger molecule. Also called a thioallyl group.

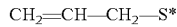

Augment, augmentation: To make greater, as in size, extent, effect, or quantity.

Bioavailability: The availability of a substance where and when needed within the body in a form which can be readily utilized for biological or biochemical purposes. The bioavailability of a substance is poor if it is not available where it is needed, or if it is in a form that can not be readily utilized, even if the substance is available in other locations or in other forms within the body.

Biothiol: Any thiol that is commonly found in biological systems. Common biothiols are cysteine, glutathione, several types of antioxidants (such as the dithiol form of lipoic acid), and several types of vitamins (such as the thiol form of from thiamine).

Bound: Confined by bonds. Not volatile. In the context of the present invention, a bound, non-volatile organosulfur group can either consist of a radical that is covalently bound to the remainder of a molecule that is large enough to be non-volatile, or it can be part of a small molecule that is non-volatile due to its being non-covalently bound to a larger molecule by forces such as hydrophobic forces.

Chelate: To detoxify a metallic ion by sequestering it in a compound.

Cysteine; CySH: a sulfur containing amino acid with the formula:

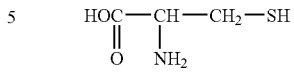

Cystine; CySSCy: cysteine disulfide. The most common form of oxidized cysteine.

The term cystine is sometimes used by others to refer to the sum of cysteine+2 cystine, for example when reporting the total cystine content of proteins. The term cyst(e)ine is used to refer to any combination of cysteine+cystine. The applicant has attempted to be rigorous in the use of these terms, but mistakes may have been made, so hopefully the particular meaning is also clear from the context. In addition, other researchers do not always distinguish between these, requiring the use of context to disambiguate between them whenever the difference between cysteine and cystine is significant.

Diallyl Disulfide; DADS: (also abbreviated as AllylSSAllyl or ASSA), the disulfide formed from two AllylMercapto radicals bonded together. Equivalent to deoxygenated allicin. In the present exposition diallyl disulfide is the model disulfide compound.

Drug: Any substance that, when taken into a living organism, may modify one or more of its functions.

Endogenous: Produced or originating from within a cell or organism.

Free radical; R*: a molecule with an unpaired electron. Free radicals are typically very reactive with molecules, with a tendency to either steal an electron, to donate an electron, or to covalently bond with another free radical. (A radical "R" within a larger molecule is a group of atoms considered as a whole that is in turn bonded to the remainder of the molecule by a single covalent bond.)

Glutathione: A tripeptide composed of the amino acids glutamate, cysteine, and glycine. Glutathione is present in biological systems in a variety of forms, the most important of which are reduced glutathione (GSH), the anion of reduced glutathione (GS⁻), the glutathiyl free radical (GS*), glutathione disulfide (GSSG), mixed glutathione disulfides (GSSR), and protein-glutathione mixed disulfides (PSSG).

The term "glutathione" used by itself usually refers to the sum of GSH and GS⁻. The term "oxidized glutathione" usually refers to GSSG (the typical end product of oxidation, even though GS* is usually the initial oxidation product). The term "total glutathione" refers to the sum of all of these.

Inactivate: To disable or decrease activity, e.g. to inactivate an enzyme.

Membrane Permeable Capable of passing through a biological membrane via simple diffusion at a moderate to high rate (e.g. in a millisecond or faster). In the contest of this invention, a compound is considered to be membrane permeable if it has a lipid to water partition ratio within the range of 0.1 to 100.

Metabolism: The entire set of chemical reactions that can occur within a living organism. This includes anabolism (the formation of more complex molecules from simple ones), catabolism (the break down of complex molecules from complex molecules to make simpler ones) and also simpler reactions, such as thiol-disulfide exchange reactions.

Mercaptan: A small molecule that contains an exposed "SH" group. Mercaptans are thiols that are typically volatile and very smelly.

Mitigate: To make less severe or less intense.

Nutraceuticals: Foods to which are added a substance to promote health.

Oxidation: The removal of an electron (or a hydrogen atom) from an atom or a molecule. Oxidation can also refer to any transformation that tends to occur when something is exposed to reactive oxygen (e.g. the formation of rust), without necessarily specifying the reaction mechanism.

Oxidized: The reaction product that tends to be produced when the reactants are exposed to reactive oxygen, such as the conversion of thiols to disulfides, typically due to the removal of electrons (or hydrogen atoms). For example, if two cysteine molecules together in solution are exposed to oxygen, they tend to eventually form a cysteine disulfide molecule (cystine).

Oxygenated: Another form of oxidation product, where an oxygen atom has been added to a molecule.

Prodrug: An inert drug that becomes active only after it is transformed or metabolized by the body.

Reactive Oxygen Species; ROS: oxygen containing molecules that are capable of producing oxidative damage to other molecules. Many, but not all, ROS are free radicals. Examples include (QP535.O1R43:33):

$H_2O_2$ (hydrogen peroxide), $*O_2^-$ (superoxide radical), $*OH$ (hydroxyl radical), $HOCl$ (hypoclorus acid), $ONOO^-$ (peroxynitrite), $O_2^1$ (singlet oxygen), $O_3$ (ozone), $*NO$ (nitric oxide), and $*NO_2$ (nitrogen dioxide).

REDST: Various researchers have found it useful to use the ratio of the square of the thiol concentration to the total disulfide concentration, $[RSH]^2/[R'SSR'']$ as a metric for the thiol-disulfide redox potential.

Reduced: The converse of oxidized. When a thiyl radical is covalently bonded to a hydrogen atom, it is said to be in its "reduced state". For example, when the terminal sulfur of a cysteinal radical is bonded to a hydrogen atom to form a cysteine molecule, it is in its reduced state. Conversely, when the hydrogen atom is removed from a cysteine molecule, it becomes a cysteinal radical.

S-AllylMercaptoCysteine; SAMC (also shown as AllylSSCy): The molecule formed by a Cysteinyl radical disulfide bonded to an AllylMercapto radical. In the present exposition SAMC is the model mixed disulfide molecule.

$$HOC-CH-CH_2-S-S-CH_2-CH=CH_2$$
$$\|\quad\ |$$
$$O\ \ NH_2$$

Sub-optimal: Below by 3% or more from the level that can be statistically shown to be optimal for this parameter across a population. For example, a sub-optimal level could be correlated with pathology, a disease state, the condition of old age, or a reduced life expectancy.

Sulfur Amino Acids; SAA: typically the sum of cysteine, cystine, methionine (constituents of proteins), and sulfur containing amino acid molecules such as homocysteine and taurine. Because they are amino acids, these molecules are too polar to be able to freely diffuse through biological membranes.

Super-optimal: Above by 3% or more from the level that can be statistically shown to be optimal for this parameter across a population. For example, a super-optimal level could be correlated with pathology, a disease state, the condition of old age, or a reduced life expectancy.

Thiol; RSH: Any molecule that includes one or more terminal sulfhydrate (SH) group.

Thiol/Disulfide Redox Status: The degree to which thiols are oxidized to disulfides within an environment (e.g. within blood plasma). This can be expressed as a simple ratio of their concentrations, or by the inverse ratio (e.g. the [disulfide]/[thiol] ratio) or by a more complex equation such as REDST. Because this varies within an organism, frequently a specified type or class of thiol or disulfide within a specific environment is assayed or otherwise specified (e.g. plasma [cystine]/[total thiol]).

Thiosulfinate: An organosulfur molecule of the form RS(O)SR'. A thiosulfinate can be regarded as an oxygenated disulfide. For example allicin, AS(O)SA, can be regarded as oxygenated diallyl disulfide, ASSA, and can be produced by exposing ASSA to the oxidant hydrogen peroxide, $H_2O_2$ (as shown in US2005/0260250A1).

Total Cystine The sum of cysteine+2 cystine (e.g. the total quantity of cysteinal residues in the sample).

Total Disulfide Concentration: The sum of the disulfide concentration plus the mixed disulfide concentration, including all of the types of disulfides and mixed disulfides that are present in the sample. Unless otherwise clear from the context, the more simple term "disulfide" is sometimes used within this specification as a shorthand term for "total disulfide".

Volatile: Evaporating readily at normal temperatures and pressures.

2. REFERENCES

For articles contained in books, the first listing (typically by Dewey decimal number or ISBN number) contains identification information for the book and the actual reference(s) are the listings for the article(s) or pages that follow.

AACID12:33; W. B. Yao et al; Protective effect of glucose-cysteine adduct on in situ perfused liver; Amino Acids 12:33.

AEMB543:191; W. Droge; Oxidative Stress and Aging; Advances in Experimental and Medical Biology 543:191.

AJM91:3 C-140S; W. Droge et al. Modulation of Lymphocyte Functions and Immune Response by Cysteine and Cysteine Derivatives; The American Journal of Medicine 91:3C-140S.

AJCN74:756; M. Buono et at; Total Sulfur Amino Acid Requirement in Young Men as Determined by Indicator Amino Acid Oxidation; American Journal of Clinical Nutrition 74:756.

AJRCCM162:1539; A. M. Cantin et al; Albumin-mediated Regulation of Cellular Glutathione and Nuclear Factor Kappa B Activation; American Journal of Respiratory and Critical Care Medicine 162:1539.

AMR6:78; Taurine; Alternative Medicine Review 6:78.

ANBC200:218; M. A. Mansoor et al; Determination of the in vivo redox status of cysteine, cysteinylglycine, homocysteine, and glutathione in human plasma; Analytical Biochemistry 200:218.

ANYAS1043; J. W. Baynes et al. 2005; The Maillard Reaction; Annals of the New York Academy of Sciences Volume 1043; The New York Academy of Sciences, New York, N.Y.

ANYAS1043:9; S. Rahbar; The Discovery of Glycated Hemoglobin; (in ANYAS1043).

ANYAS1043:845; B. S. Szwergold, et al; Transglycation—A Potential New Mechanism for Deglycation of Schiff's Bases; (in ANYAS1043).

APJCP4:7; M. Khan et al; Magnitude of Arsenic Toxicity in Tube-well Drinking Water in Bangladesh and Its Adverse Effects on Human Health Including Cancer: Evidence from a Review of the Literature; Asian Pacific Journal of Cancer Prevention 4:7.

ARB52:711; A. Meister and M. Anderson; Glutathione; Annual Review of Biochemistry 52:711.

ARCHIM138:356; P. R. Greipp; Hyperpigmentation Syndromes (Diffuse Hypermelanosis); Archives of Internal Medicine 138:356.

ARR1:257; W. Droge; The Plasma Redox State and Ageing; Ageing Research Reviews 1:257.

ARTSC8:452; C. Chen et al; Atherogenicity and Carcinogenicity of High-Arsenic Artesian Well Water; Arterisclerosis 8:452).

ATOX71:730; T. Ochi; Arsenic compound-induced increases in glutathione levels in cultured Chinese hamster V79 cells and mechanisms associated with changes in gamma-glutamylcysteine synthase activity, cystine uptake and utilization of cysteine; Archives of Toxicology 71:730.

ATOX79:183; T. Hayakawa, et al; A new metabolic pathway of arsenite: arsenic-glutathione complexes are substrates for human arsenic methyltransferase Cyt19; Archives of Toxicology 79:183.

BBA46:217; J. Bremer and D. Greenberg; Enzymic Methylation of Foreign Sulfhydryl Compounds; Biochimica et Biophysica Acta 46:217.

BBA628:241; P. T. Pisciotto and J. H. Graziano; Induction of Mucosal Glutathione Synthesis by Arsenic; Biochemica et Biophysica Acta 628:241.

BBRC242:1; I. Cotgreave and R. Gerdes; Recent Trends in Glutathione Biochemistry—Glutathione-Protein Interactions: A Molecular Link between Oxidative Stress and Cell Proliferation?; Biochemical and Biophysical Research Communications 242:1.

BIJ63:514; E. D. Wills; Enzyme Inhibition by Allicin, the Active Principle of Garlic; Biochemical Journal 63:514.

BIJ105:891; J. Crawhall and S. Segal; The intracellular Ratio of Cysteine to Cystine in Various Tissues; Biochemical Journal 105:891.

BLOOD92:59; V. Hack et al; The redox state as a correlate of senescence and wasting and as a target for therapeutic intervention; Blood 92:59.

BLOOD93:268; J. Dai, et al; Malignant Cells Can Be Sensitized to Undergo Growth Inhibition and Apoptosis by Arsenic Trioxide Through Modulation of the Glutathione Redox System; Blood 93:268.

BLOOD97:3931; O. Sondet; Mitochondria-targeting drugs arsenic trioxide and lonidamine bypass the resistance of TPA-differentiated leukemic cells to apoptosis; Blood 97:3931.

BLOOD98:805; J. M. Grad et al; Ascorbic acid enhances arsenic trioxide-induced cytotoxicity in multiple myeloma cells; Blood 98:805.

BMCCC6:155; G. G. Gyamlani et al; Acetaminophen toxicity: suicidal vs accidental; BioMed Central Critical Care 6:155.

BP23:1133; L. F. Chasseaud; Reaction with electrophiles after enzyme-catalysed deacetylation of N-acetylcysteine; Biochemical Pharmacology 23:1133.

BST23:S136; I. Das et al; Nitric Oxide Synthase is a Unique Mechanism of Garlic Action; Biochemical Society Transactions 23:S136.

BWHO78:1093; A. H. Smith, et al; Contamination of drinking-water by arsenic in Bangladesh: a public health emergency; Bulletin of the World Health Organization 78:1093.

CBEP12:350; M. L. Neuhouser et al; Fruits and Vegetables Are Associated with Lower Lung Cancer Risk Only in the Placebo Arm of the beta-Carotene and Retinol Efficacy Trial (CARET); Cancer Epidemiology, Biomarkers & Prevention 12:350.

CCA67:417; H. Birwe and A. Hesse; High-performance liquid chromatographic determination of urinary cysteine and cystine; Clinica Chimica Acta 67:417.

CCA136:75; H. B. Mortensen et al; Glucosylation of human hemoglobin A. Dynamic variation in HbA1c described by a biokinetic model; Clinica Chimica Acta 136:75.

CCHEM51:5; W. Herrmann et al; Disturbed Homocysteine and Methionine Cycle Intermediates S-Adenosylhomocysteine and S-Adenosylmethionine Are Related to Degree of Renal Insufficiency in Type 2 Diabetes; Clinical Chemistry 51:5.

CCP52:47; X. Hu et al; Arsenic trioxide induces apoptosis in cells of MOLT-4 and its daunorubicin-resistant cell line via depletion of intracellular glutathione, disruption of mitochondrial membrane potential and activation of caspase-3; Cancer Chemotherapy and Pharmacology 52:47.

CCR8:3658; N. Bahlis et al; Feasibility and Correltaes of Arsenic Trioxide Combined with Ascorbic Acid-mediated Depletion of Intracellular Glutathione for the Treatment of Relapsed/Refractory Multiple Myeloma; Clinical Cancer Research 8:3658.

CG9:131; V. L. Sparnins et al; Effects of organosulfur compounds from garlic and onions on benzo[a]pyrene-induced neoplasia and glutathione S-transferase activity in the mouse; Carcinogenesis 9:131.

COCNMC2:227; W. Droge; Cysteine and glutathione in catabolic conditions and immunological dysfunction; Current Opinion in Clinical Nutrition and Metabolic Care 2:227.

CR61:725; H. Shirin et al; Antiproliferative Effects of S-Allylmercaptocysteine on Colon Cancer Cells When Tested Alone or in Combination with Sulindac Sulfide; Cancer Research 61:725.

CRT6:102; N. Scott, et al; Reactions of Arsenid (III) and Arsenic (V) Species with Glutathione; Chemical Research in Toxicology 6:102.

CRT10:27; M. Styblo et al; Comparative Inhibition of Yeast Glutathione Reductase by Arsenicals and Arsenothiols; Chemical Research in Toxicology 10:27.

E185.96.D368; S, and E. Delany with A. Hearth, 1994; The Delany Sisters'Book of Everyday Wisdom; Kodansha International, New York, N.Y.

E185.96.D368:107; The Order of the Day (in E185.96.D368).

EG37:1331; W. Droge; Aging-related changes in the thiol/disulfide redox state: implications for the use of thiol antioxidants; Experimental Gerontology 37:1331.

EHP108:617; A. H. Smith et al; Arsenic-Induced Skin Lesions among Atacameno People in Northern Chile Despite Good Nutrition and Centuries of Exposure; Environmental Health Perspectives 108:617.

EHP112:1104; S. Mitra, et al; Nutritional Factors and Susceptibility to Arsenic Caused Skin Lesions in West Bengal, India; Environmental Health Perspectives 112:1104.

EJB2:327; P. Jocelyn; The Standard Redox Potential of Cysteine-Cystine from the Thiol-Disulfide Exchange Reaction with Glutathione and Lipolic Acid; European Journal of Biochemistry 2:327.

EJCI30:915; S.C. De Rosa et al; N-acetylcysteine replenishes glutathione in HIV infection; European Journal of Clinical Investigation 30:915.

EJCELLB68:47; J. F. Beaver et al; A decrease in intracellular glutathione concentration precedes the onset of apoptosis in murine thymocytes; European Journal of Cell Biology 68:47.

EMM21:383; T. Das, et al; Modification of Clastogenicity of Three Known Clastogens by Garlic Extract in Mice in Vivo; Environmental and Molecular Mutagenesis 21:383.

ENVTP8:227; S. Maiti and A. J. Chatterjee; Differential response of cellular antioxidant mechanism of liver and kidney to arsenic exposure and its relation to dietary protein deficiency; Environmental Toxicology and Pharmacology 8:227.

FEBSJ273:3346; A. Kawakami et al; Identification and characterization of oxidized human serum albumin; FEBS Journal 273:3346.

FRBM24:789; S. Mendiratta et al; Erythrocyte Ascorbate Recycling: Antioxidant Effects in Blood; Free Radicals in Biology and Medicine 24:789.

HTOX8:99; R. L. Shannon and D. S. Strayer; Arsenic-induced Skin Toxicity; Human Toxicology 8:99.

IJEP27:871; D. N. G. Mazumder et al; Arsenic levels in drinking water and the prevalence of skin lesions in West Bengal, India; International Journal of Epidemiology 27:871.

JAFC53:1974; L. Lawson and Z. Wang; Allicin and Allicin-Derived Garlic Compounds Increase Breath Acetone through Allyl Methyl Sulfide: Use in Measuring Allicin Bioavailability; Journal of Agricultural and Food Chemistry 53:1974.

JBC268:5535; H. Zhang et al; Structural Requirements for the Binding of Modified Proteins to the Scavenger Receptor of Macrophages; The Journal of Biological Chemistry 268: 5535.

JBC275:33404; S. V. Kala et al; The MRP2/cMOAT Transporter and Arsenic-Glutathione Complex Formation Are Required for Biliary Excretion of Arsenic; The Journal of Biological Chemistry 275:33404.

JCHROMA1032:109; E. Bald et al; Analysis of plasma thiols by high-performance liquid chromatography with ultraviolet detection; Journal of Chromatography A 1032: 109.

JCHROMB674:23; C. S. Yang et al; Effect of ageing on human plasma glutathione concentrations as determined by high-performance liquid chromatography with fluorimetric detection; Journal of Chromatography B Biomedical Applications 674:23.

JCI63:53; E. Orringer and M. Roer; An Ascorbate-Mediated Transmembrane-Reducing System of the Human Erythrocyte; Journal of Clinical Investigation 63:53.

JCPHY133:330; T. Ishii et al; Regulation of Glutathione Levels in Mouse Spleen Lymphocytes by Transport of Cysteine; Journal of Cellular Physiology 133:330.

JESH38A:141; D. N. G. Mazumder; Chronic Arsenic Toxicity: Clinical Features, Epidemiology, and Treatment: Experience in West Bengal; Journal of Environmental Science and Health; A38:141.

JFCA2:327; G. Wierzbicka et al; Glutathione in Food; Journal of Food Composition and Analysis 2:327.

JID185:1115; P. Villa et al; Glutathione protects mice from lethal sepsis by limiting inflammation and potentiating host defense; Journal of Infectious Diseases 185:1115.

JLRPAW30:1703; R. Barnhart et al; Concentration-dependent antioxidant activity of probucol in low density lipoproteins in vitro: probucol degradation preceeds lipoprotein oxidation; Journal of Lipid Research 30:1703.

JMM78:55; R. Breitkreutz et al; Improvement of immune functions in HIV infection by sulfur supplementation: two randomized trials; Journal of Molecular Medicine 78:55.

JN114:2241; M. Friedman et al; Nutritional Improvement of Soy Flour; Journal of Nutrition 114:2241.

JN131:985 S; B. Lau; Suppression of LDL Oxidation by Garlic; Journal of Nutrition 131, supplement 3S:985S.

JN134:128; F. Mariotti et al; Acute ingestion of dietary proteins improves post-exercise liver glutathione in rats in a dose-dependent relationship with their cysteine content; Journal of Nutrition 134:128.

JSR65:165; S. Blair et al; Oral L-2-Oxo-4-thiazolidine Reduces Bacterial Translocation after Radiation in the Fischer Rat; Journal of Surgical Research 65:165.

MHPY66:698; B. S. Szwergold; alpha-Thiolamines such as cysteine and cysteamine act as effective transglycating agents due to formation of irreversible thiazolidine derivatives; Medical Hypotheses 66:698.

MOPM60:302; J. Liu et al; Overexpression of Glutathione S-Transferase II and Multidrug Resistance Transport Proteins Is Associated with Acquired Tolerance to Inorganic Arsenic; Molecular Pharmacology 60:302.

N207:1269; R. Hamm and K Hoffman; Changes in the Sulphydryl and Disulfide Groups in Beef Muscle Proteins During Heating; Nature 207:1269.

NYTIMES2007:0121A; G. O'Mullan et al; Sniffing Out the Truth; The New York Times, Jan. 21, 2007.

NYTIMES2007:0121 B; L. Turin; What You Can't Smell Will Kill You; The New York Times, Jan. 21, 2007.

PHYRES3:50; S, Nakagawa et al; Prevention of Liver Damage by Aged Garlic Extract and Its Components in Mice; Phytotherapy Research 3:50.

PM56:668; F. Jung et al; Effect of Different Garlic Preparations on the Fluidity of Blood, Fibrolytic activity, and Peripheral Microcirculation in comparison with placebo; Planta Medica 56:668.

PM59:A688; L. Lawson and Z. Wang; Pre-Hepatic Fate of the Organosulfur Compounds Derived from Garlic (*Allium sativum*); Planta Medica 59:A688.

PNAS98:1643; S. X. Liu et al; Induction of oxyradicals by arsenic: Implication for mechanism of genotoxicity; Proceedings of the National Academy of Science 98:1643.

PTRSB360:2355; W. Droge; Oxidative stress and ageing: is ageing a cysteine deficiency syndrome? Philosophical Transactions of the Royal Society 360:2355.

QD305.S3C48; Edited by S. Patai and Z. Rappoport 1993; Supplement S: The Chemistry of Sulphur-containing Functional Groups; John Wiley & Sons, New York, N.Y.

QD305.S3C48:633; R. Singh and G. Whitesides; Thiol-Disulfide Interchange (in QD305.S3C48).

QD305.S3S14; Edited by Z. Alfassi, 1999; S-Centered Radicals; John Wiley & Sons, New York, N.Y.

QD305.S3S14:289; P. Wardman; Thiyl Radicals in Biology: Their Role as a "Molecular Switch" Central to Cellular Oxidative Stress (in QD305.S3S14).

QH545.A77; Committee on Medical and Biologic Effects of Environmental Pollutants; Arsenic; National Academy of Sciences, Washington, D.C.

QH545:A77:4; Chemistry of Arsenic (in QH545.A77).

QH545.A77:117; Biologic Effects of Arsenic on Plants and Animals (in QH545.A77).

QP141.N48; H. Newstrom, 1993; Nutrients Catalog; McFarland & Company Inc. Jefferson, N.C.

QP141.N48:249; Cysteine (in QP141.N48).

QP535.O1R43; Edited by D. L. Gilbert and C. A. Colton; Reactive Oxygen in Biological Systems, 1999; Kluwer Academic, New York, N.Y.

QP535.O1R43:33; R. Huie and P. Neta; Chemistry of Reactive Oxygen Species (in QP535.O1R43).

QP551.P6976; C. Bodwell et al; Protein Quality in Humans: Assessment and in vitro Estimation; AVI Publishing Company, Inc., Westport, Conn.

QP551.P6976:3; N. Serimshaw; Nutritional Significance of Protein Quality: A Global View (in QP551.P6976).

QP551.P6976:98; R. Bressani et al; A Short-Term Procedure to Evaluate Protein Quality in Young and Adult Human Subjects (in QP551.P6976).

QP552.P4S93; Chaired by D. Parsons, 1976; Peptide Transport and Hydrolysis; Van Gorcum, Assen, The Netherlands.

QP552.P4S93:151; Y. Kim; Intestinal mucosal hydrolysis of proteins and peptides (in QP552.P4S93:151).

QP552.G58F585; edited by J. Vina, 1990; Glutathione: Metabolism and Physiological Functions; CRC Press, Boca Raton, Fla.

QP552.G58F585:125; R. Freedman; The Formation of Disulfide Bonds in the Synthesis of Secretory Proteins: Properties and Role of Protein Disulfide-Isomerase (in QP552.G58G585).

QP552.G58F85; A. Larsson et al, 1983; Functions of Glutathione—Biochemical, Physiological, Toxicological, and Clinical Aspects; Raven Press, New York, N.Y.

QP552.G58F85:205; T. E. Creighton; Pathways and Energetics of Protein Disulfide Formation (in QP552.G58F85).

QP552.G58G54; Edited by N. Taniguchi et al, 1989; Glutathione Centennial: Molecular Perspectives and Clinical Implications; Academic Press, New York, N.Y.

QP552.G58G54:57; N. Tateishi and Y. Sakamoto; Regulation of Glutathione Level in Primary Cultured Hepatocytes (in QP552.G58G54).

QP552.G58G54:73; H. Gilbert; Thermodynamic and Kinetic Constraints on Thiol/Disulfide Exchange Involving Glutathione Redox Buffers (in QP552.G58G54).

QP552.G58G54:407; S. Bannai et al; Regulation of Glutathione Level by Amino Acid Transport (in QP552.G58G54).

QP601.E515; Edited by W. Jakoby, 1980; Enzymatic Basis of Detoxification Volume II; Academic Press, New York, N.Y.

QP601.E515:131; R. Weisiger and W. Jakoby; S-Methylation: Thiol S-Methyltransferase (in QP601.E515).

QP601.W38V3; J. L. Webb; Enzyme and Metabolic Inhibitors—Volume III, 1966; Academic Press, New York, N.Y.

QP601.W38V3:595; Arsenicals (in QP601.W38V3).

QP606.G59G59; N. Vermeulen et al, 1996; Glutathoine S-Transfetases: Structure, Function and Clinical Implications; Taylor & Francis Ltd., London, England.

QP606.G59G59:199; T. Ishikawa and K. Akimaru; Transport of Glutathone S-Conjugates from Cancer Cells: Function and Structure of the GS-X Pump (in QP606.G59G59).

QP722.A8A586; Edited by L. Packer, et al, 2002; The Antioxidant Vitamins C and E; AOCS Press, Champaign, Ill.

QP722.A8A586:133; L. Packer and U. Obermuller-Jevic; Vitamin E: An Introduction (in QP722.A8A586).

R850.A1A3V459; edited by Jackson et al, 1999; Impact of Food Processing on Food Safety; Kluwer Academic, New York, N.Y.

R850.A1A3V459:161; G. Sarwar et al; Influence of Feeding Alkaline/Heat Processed Proteins on Growth and Protein and Mineral Status of Rats (in R850.A1A3V459:161).

RA1231.A7M44; A. A. Meharg, 2005; Venomous Earth—How arsenic caused the world's worst mass poisoning; Macmillan, New York, N.Y.

RA1231.A7M44:170; JOI BANGLA! (in RA1231.A7M44).

RA1231.A7N38; Subcommittee on Arsenic in Drinking Water; Arsenic in Drinking Water, 1999; National Academy Press, Washington, D.C.

RA1231.A7N38:150; Disposition of Inorganic Arsenic (in RA1231.A7N38).

RA1231.A7N38:177; Biomarkers of Arsenic Exposure (in RA1231.A7N38).

RB170.H36; E. Cadenas and L. Packer, 2002; Handbook of Antioxidants; Marcel Dekker, Inc. New York, N.Y.

RB170.H36:235; W. G. Seims et al; Oxidative Breakdown of Carotenoids and Biological Effects of Their Metabolism (in RB170.H36).

RB170.O96; Edited by C. Pasquier, R. Oliver, C. Auclair and l. Packer, 1994; Oxidative Stress, Cell Activation and Viral Infection; Birkhauser Verlag, Basel Switzerland.

RB170.O96:101; A. Meister; The Antioxidant Effects of Glutathione and Ascorbic Acid (in RB170.O96).

RB170.O96:285; W. Droge et al; Abnormal Redox Regulation in HIV Infections and other Immunodeficiency Diseases (in RB170.O96).

RM666.G15K6313; H. P. Koch and L. D. Lawson, 1996; GARLIC The Science and Therapeutic Application of *Allium sativum* L. and Relates Species; Williams & Wilkins, Baltimore, Md.

RM666.G15K6313:190; H. P. Koch and L. D. Lawson; Antioxidant Effects: Active Compounds (in RM666.G15K6313).

RR2:392; P. Alexander et al; Mode of Action of Some Substances Which Protect against the Lethal Effects of X-Rays; Radiation Research 2:392.

S97:356; E. S. G. Barron, T. P. Singer; Enzyme Systems Containing Active Sulphydryl Groups. The Role of Glutathione; Science 97:356.

TAP154:287; R. A. Zakharyan and H. V. Aposhian; Arsenite Methylation by Methylvitamin B12 and Glutahtione Does Not Require an Enzyme; Toxicology and Applied Pharmacology 154:287.

TAP183:99; E. M. Brambila et al; Chronic Arsenic-Exposed Human Prostate Epithelial Cells Exhibit Stable Arsenic Tolerance: Mechanistic Implications of Altered Cellular Glutathione and Glutathione S-transferase; Toxicology and Applied Pharmacology 183:99.

TAP206:198; CJ Chen et al; Biomarkers of exposure, effect, and susceptibility of arsenic-induced health hazards in Taiwan; Toxicology and Applied Pharmacology 206:198.

TL37:41; M. Vahter and E. Marafante; Effects of Low Dietary Intake of Methionine, Choline or Proteins on the Biotransformation of Arsenite in the Rabbit; Toxicology Letters 37:41.

TL69:15; R. White et al; Toxicity Evaluations of L-cysteine and Procysteine, a Cysteine Prodrug, Given Once Intravenously to Neonatal Rats; Toxicology Letters 69:15.

TOXICOL79:195; H. Huang, et al; Glutathione as a cellular defense against arsenite toxicity in cultured Chinese hamster ovary cells; Toxicology 79:195.

TOXL70:101; M. R. Gomez et al; Attenuation of acetaminophen hepatotoxicity in mice as evidence for the bioavailability of the cysteine in D-glucose-L-cysteine in vivo; Toxicology Letters 70:101.

TOXSCI70:183; M. Schuliga et al; Upregulation of Glutathione-Related Genes and Enzyme Activities in Cultured Human Cells by Sublethal Concentrations of Inorganic Arsenic; Toxicological Sciences 70:183.

TOXSCI91:70; C. Kojima et al; Chronic Exposure to Methylated Arsenicals Stimulates Arsenic Excretion Pathways and Induces Arsenic Tolerance in Rat Liver Cells; Toxicological Sciences 91:70.

TP371.8P74; E. Josephson et al; Preservation of Food by Ionizing Radiation, Volume I; CRC Press Inc., Boca Raton, Fla.

TP371.8P74:279; J. Deihl; Radiolytic Effects in Foods (in TP371.8P74).

TP453.P7F68; Edited by S. Nakai and H. Modler 1996; Food Proteins: Properties and Characterization; VHC Publishers, New York, N.Y.

TP453.P7F68:23; R. Ludescher; Physical and Chemical Properties of Amino Acids and Proteins (in TP453.P7F68).

TP453.P7F68:281; M. Friedman; Nutrition (in TP453.P7F68)

TX589.F46131:17; G. Fenaroli; Fenaroli's Handbook of Flavor Ingredients; CRC Press, Cleveland Ohio, 1975.

US002432797; R. A. Peters et al; Organic Thiol Antitoxic Agents; U.S. Pat. No. 2,432,797.

US005334671A; P. C. Ulrich et al; Amino Acids Useful as Inhibitors of the Advanced Glycosylation of Proteins; U.S. Pat. No. 5,334,617.

US005451412A; G. Bounous et al; Biologically Active Undenatured Whey Protein Concentrate as Food Supplement; U.S. Pat. No. 5,451,412.

US006896899B2; H. B. Demopolos et al; Pharmaceutical Preparations of Glutathione and Methods of Administration Thereof; U.S. Pat. No. 6,896,899.

US2004/0235946A1; D. M. Ott; Organosulfur Prodrugs for the Prevention and Treatment of Infectious Diseases and Pathologic Immune System Response; US Patent Application Publication US2004/0235946A1.

US2005/0260250A1; D. M. Ott; Medicinal Products Incorporating Bound Organosulfur Groups; US Patent Application Publication US2005/0260250A1.

US2006/0269488A1; D. M. Ott; Personal Care and Medicinal Products Incorporating Bound Organosulfur Groups; US Patent Application Publication US2006/0269488A1.

3. DESCRIPTION OF THE PUBLISHED ART 3.1 Biothiols in Health and Disease

Just as water has been determined to be essential for life on earth, biothiols are known to be essential to all forms of life that have evolved on this planet. Cysteine (including the cysteine in proteins and peptides such as glutathione) is the overwhelming biothiol, typically providing well over 90% of the total thiol content of the organism. For animals, the primary source of cysteine is dietary protein, which contains the amino acids cysteine, cysteine disulfide (cystine), and methionine (which can metabolize to cysteine).

3.1.1 Cysteine—Amino Acid, Biothiol, and Glutathione Precursor

Cysteine is a sulfur containing amino acid which is an important constituent of proteins. In fact, the SH group of cysteine when ionized (i.e. to CyS$^-$) is the most reactive group in proteins (TP453.P7F68:23). The active site of many enzymes (e.g. proteases) involves cysteine, where the reactivity of the CyS$^-$ group contributes significantly to the activity of the enzyme.

Cysteine shares many properties with other biothiols which have a terminal "SH" group. It is able to participate in thiol-disulfide exchange reactions with almost all types of disulfides, resulting in a wide variety of mixed disulfides (QD305.S3C48:633). Thiol-disulfide exchange reactions allow the formation of disulfide bonds (which are covalent bonds, so they are quite strong) and their later separation, without significant energy involvement other than the thermal energy that brings them together or apart.

The formation of the tertiary structure of proteins ("conformation", from protein folding) depends upon the proper formation of disulfide bonds between pairs of cysteines within the polypeptide chain of the protein. These disulfide bonds can stabilize or regulate the protein structure and activity. Disulfide bonds can also link adjacent proteins, providing structure to tissues. Disulfide bonds also affect the stiffness of the eye lens, and the excessive formation of disulfide bonds is implicated in the development of cataracts (BBRC242:1).

Many types of proteins are "redox regulated" (ARR1:257), with their function and/or activity depending both upon the current conformation and also upon whether critical SH groups on the protein are in the in thiol form (PSH), or are in the in thiolate form (PS$^-$), or are currently blocked (e.g. PSSG)

Cysteine tends to auto-oxidize to cystine (CySSCy) in the presence of oxygen. Inside cells, the "reductive" environment provided by the maintenance of reduced glutathione (by the enzyme glutathione reductase) tends to keep the cysteine in its reduced form (CySH), but in the more oxidative extracellular environment the disulfide cystine readily forms. When attempting to separately assay cysteine and cystine in biological samples, special precautions must be used to prevent cysteine oxidation (CCA67:417, JCHROMA1032:109). For example, the thiol status of plasma can changes within seconds after blood collection (ANBC200:218).

3.1.1.1 Dietary Sources Cysteine and Other Sulfur Amino Acids

Cysteine deficiency may be common even in people who eat "Enough" protein. Many sources of dietary protein have a low content of cyst(e)ine and methionine (another amino acid that can be metabolized to cysteine in vivo, e.g. by the liver). People who don't eat much animal protein are at risk because most other foods have a low content of sulfur amino acids.

The Nutrients Catalog (QP141.N48:249) lists the amino acid contents of a wide variety of food sources (in mg per 100 g, also listed here for typical foods). The cyst(e)ine content of animal tissue protein sources, seeds and some types of legumes and some types of nuts tend to range from ~400 (fried chicken) down to ~200 (beef lunch meat). Cereals (corn flakes, wheat flakes, shredded wheat) have ~200. Cheeses, evaporated milk, tofu, and some types of beans and nuts tend to be in the range of 120 down to 40. Fruits and vegetables tend to be in the range of 30 down to 10. Beverages, foods with a high water content, some processed foods, and some fruits have less than 10 (e.g. orange juice, watermelon, cucumbers, pumpkin, canned carrots, and apples). As these figures indicate, animal protein typically has ~3 times the cyst(e)ine content of cheeses, nuts, and beans and ~10 times that of fruits and vegetables.

In 2001, it was reported that the current recommendation for daily dietary sulfur amino acid consumption were low by almost a factor of two (13 mg/kg instead of 25 mg/kg) due to an arithmetic error when the requirements were determined experimentally in 1955 (AJCN74:756). Therefore, a 70 kg person should actually be consuming 1750 mg of sulfur amino acids per day (of which approximately ½ will be cyst(e)ine and ½ will be methionine). Another problem with the way that dietary sulfur amino acid requirements were determined is that the experiments were based on "nitrogen balance" which only measures the amount of the amino acid that is needed for protein formation (weight maintenance) and does not take into account other biological requirements for cysteine (such as the synthesis of glutathione, taurine, and sulfate).

The 1960s were years of concern for protein quality, with predictions of an impending "protein crisis" in developing countries. But the global perception of world food and nutrition problems abruptly changed in 1971, when a joint FAO/WHO "Expert Committee on Energy and Protein Requirements" concluded that the focused effort should be on meeting the caloric requirements instead. "It became fashionable to emphasize the deficiency of energy in the diets of low-income populations and to point out that if this were corrected, protein needs, as indicated by the 1971 committee report would be met" (QP551.P6976:3).

The need for dietary sulfur amino acid consumption continues to receive little emphasis in dietary recommendations, and in the opinion of the applicant, it is much too easy for people who think that they are eating well to actually not be consuming enough sulfur amino acids. Regarding dietary protein, the newly published "Dietary Guidelines for Americans 2005" only briefly mentions proteins (and not individual amino acid requirements at all) and states that "most Americans are already consuming enough. . . . As such, protein consumption, while important for nutritional adequacy, is not a focus of this document." In the opinion of the applicant, by limiting their consideration to "most Americans", these guidelines are not providing guidance to some of those who need it most.

Their recommendations for fruits, vegetables, and other nutrients seem reasonable in most respects, but what percentage of the American population will actually consume 3 cups of milk a day? And what about those who don't?Those who avoid milk consumption are specifically recommended to find other sources rich in calcium, potassium, magnesium, zinc, iron, riboflavin, vitamin A, folate, and vitamin D, but protein is not mentioned in the list. In the section on "Vegetarian Choices", it is stated that "½ ounce of nuts or ¼ cup of legumes is considered equivalent to 1 ounce of meat, poultry or fish", which is probably correct in terms of total protein content, but does not take into account that the bioavailable content of SAA in nuts and legumes is lower. For example, their recommended 5.5 ounces of meat would contain ~500 mg of SAA, but their "equivalent" of 2.75 ounces of nuts would contain only ~250 mg per day (not very much compared to the 1750 mg that is needed).

Glutathione in food varies dramatically, such that well fed Americans can have a 40:1 range in its consumption (JFCA2:327). However, dietary glutathione probably has no special significance relative to other sources of cysteine because it is likely to be broken down to its constituent amino acids during digestion. The glutathione inside cells is created from its constituent amino acids (glutamate, cysteine, and glycine). Of these, cysteine is almost always the limiting amino acid, because glutamate and glycine are relatively common in foods.

Dietary taurine comes exclusively from animal sources (there is no taurine in plants), but the body can produce taurine if necessary from excess cysteine. In other words, without enough taurine consumption, or extra cysteine consumption (beyond the requirements for protein and glutathione synthesis), taurine deficiency can occur. One effect of taurine deficiency is impaired cholesterol metabolism, which can lead to cardiovascular disease (AMR6:78).

A particularly good source of dietary cyst(e)ine is whey protein, which has been shown to increase glutathione levels, with a wide variety of associated health benefits (US005451412A). It has also been claimed that the undenatured cystine in whey protein is more bioavailable than other dietary sources of cyst(e)ine (US005451412A).

Dietary alliums (e.g. garlic and onions) are a good dietary source of cyst(e)ine, but their unpleasant side effects when consumed in other than small quantities limit their ability to serve as a primary source of cyst (e) ine.

3.1.2 Anti-Nutritional Factors 3.1.2.1 Cysteine Loss from Food Processing and Cooking.

The sulfhydryl and disulfide groups of proteins (i.e. the cysteine and cystine) are the most vulnerable amino acids to food processing, and have been shown to be easily damaged by heat during cooking. Heating above 30 degrees C. causes the progressive denaturation of the protein, and heating above 70 degrees C. causes the progressive irreversible destruction of cyst(e)ine (N207:1269). Interestingly, although cooking increases the digestibility of protein in general (due to the thermal unfolding of the proteins), given that cyst(e)ine is commonly the limiting amino acid in foodstuffs the damage to the cyst(e)ine can lower the net protein quality of cooked food.

Foods are treated with heat and alkali for many purposes such as to sterilize/pasteurize, to improve flavor or texture, to destroy toxic or anti-nutritional factors, to promote desirable physical properties, and to solubilize proteins (R850.A1A3V459:161). The formation of lysinoalanine (LAL) mainly via the reaction between the lysine and cysteine residues that occurs during heat treatment in the presence of alkaline not only results in cysteine loss, but the LAL itself is toxic and can cause kidney damage. Experimentally, the alkaline treatment with 0.1N NaOH at room temperature for 1 hour followed by heat treatment at 75 degrees C. for 3 hours and then neutralization with 10N HCl resulted in the loss of 20% of the lysine and 75% of the cysteine, along with the HPLC detectable formation of LAL (R850.A1A3V459:161). The anti-nutritional factors formed during alkaline/heat treatment also caused a reduction of weight gain of rats of 25% compared to those fed untreated diets (R850.A1A3V459:161). Other chemical treatments of foods that affect the cysteine content include browning (e.g. the Maillard reaction), acetylation, and glycosylation.

The sulfhydryl and disulfide groups of proteins are also the most easily damaged components of food from anti-microbial radiation treatment, as is shown by the 29% loss of cyst(e)ine reported for irradiated codfish (TP371.8P74:279). There is also up to a 200-fold greater sensitivity of "SH" enzymes to inactivation by irradiation relative to the "non-SH" enzymes (TP371.8P74:279). These indicate that it is probably the damage to cyst(e)ine that kills the irradiated microbes. Foods that have been sterilized for storage are also likely to be cooked prior to eating, so the cumulative loss of cyst(e)ine could be significantly greater than the figures given here.

While whey protein is an excellent source of cyst(e)ine, its bioavailable cyst(e)ine is very sensitive to denaturation from heat or mechanical shock, requiring a microfiltration process to be used during its manufacture. If not prevented, this denaturation causes a significant decrease in the ability of whey protein to raise the glutathione level (US005451412A).

3.1.2.2 Foods that Inhibit Digestive Enzymes

Legumes, especially soy beans, inhibit digestive enzymes so much that they not only have poor digestibility themselves but they also reduce the digestion of other proteins being consumed in the same meal, unless the enzyme inhibitors are completely deactivated (TP453.P7F68:281). The digestive enzymes that are secreted by the digestive system are rich in cysteine and are normally "recycled" (i.e. digested) along with the food, but the inhibitors in legumes prevent these enzymes from being successfully digested and reabsorbed, so there can be a net cysteine loss from the digestive process itself. Therefore, protease inhibitors and lectins in beans and soybean meal are found to be anti-nutritional (they actually cause a meal to become nutritionally deficient when they are consumed during an otherwise nutritionally adequate meal).

Experiments with rats show that when added to a casein (milk protein) diet, beans decrease growth, diet efficiency, protein digestibility and protein utilization. Although heat treatment (to deactivate the inhibitors) improved the nutritional value of the mixed bean-casein diet, the values were still lower that a diet of 10% casein alone (TP453.P7F68: 281). In other words, even after heat treatment, the beans were anti-nutritional.

Most commercially available soy flours have been heat treated but still retain 5-20% of the original inhibitor activity because more heat treatment would cause excessive damage to the nutritive value of soy proteins (in addition to the cyst(e)ine loss). Supplementation with cysteine or NAC prior to heat treatment deactivates the enzyme inhibitors more effectively than the heat treatment alone, allowing a lower temperature to be used and providing some cysteine supplementation. For example, adding cysteine (2% by weight) and then heating the soy flour at 65 degrees C. for 1 hour deactivates the trypsin enzyme inhibitor by over 90%, improving the protein efficiency ratio (PER) by a factor of 2.43 (JN114: 2241). In other words, without supplementation, the protein is only 41% as effective as a nutrient. Much of this PER improvement is presumably due to the cysteine supplementation, given that cyst(e)ine is typically the limiting amino acid in soy flour.

3.1.2.3 Unbalanced or Excessive Amino Acid Consumption

Unbalanced amino acid concentrations can cause a variety of anti-nutritive conditions. As an interesting side note, although rice and black beans are each incompletely balanced protein sources individually, they complement each other and can form a well balanced source of protein when consumed together in the same meal (QP551.P6976:98).

Even at the cellular level, an unbalanced amino acid concentration can cause pathology. Because cystine and glutamate share the same membrane transport system in some cell types such as fibroblasts (QP552.G58G54:407) and macrophages (RB170.096:285), glutamate competitively inhibits the cellular uptake of cystine. For macrophages, this in turn limits their ability to release the cysteine required for the stimulation of adjacent T-lymphocytes (RB170.096:285). An imbalance between extracellular glutamate and cystine is implicated in the pathology of AIDS (RB170.096:285), the lethality of lung cancer (RB170.096:285), and the progression of aging (ARR1:257).

3.1.2.4 The Regulation of the Digestive Uptake of Amino Acids

In mammals, the digestion of proteins (hydrolysis) is performed by protease and peptidase enzymes following the denaturation of the proteins by stomach acid. After the enzymes in the stomach and the interior of the intestine break the proteins into small fragments (peptides), the smallest of which (e.g. dipeptides, each consisting of a pair of amino acids) are then preferentially taken up from the intestinal lumen by the "brush boarder" cells that line the small intestine (QP552.P4S93:151). The following is a simplified description of this process.

Within these brush boarder cells, multiple "dipeptidase" enzymes which are each specific to the second amino acid of the dipeptide (and are feedback regulated by the concentration of this amino acid in the cytosol) can further break down the dipeptide into its two amino acids. The individual amino acids then leave the brush boarder cells on the other side and enter the portal vein of the blood stream.

The transport of the amino acids on the blood system side of the cell is actually bidirectional, therefore the concentration of each amino acid within the cell is in rough equilibrium with its concentration in the blood stream. This automatically inhibits the specific dipeptidase that produces this amino acid from the dipeptides that contain it as the second peptide. (Because there are 20 types of amino acids commonly found in proteins, there could be ~400 types of dipeptides in food, yet this scheme allows the regulation of amino acid uptake with only ~20 dipeptidases being needed.)

The transport of the dipeptides on the intestinal side of the brush boarder cells in also bi-directional, therefore the concentration of dipeptides inside the cell approximates the concentration in the lumen of the small intestine. This automatically returns to the lumen (eventually) from the cell the excess of those dipeptides for which the dipeptidase is inhibited, because as the other dipeptides are digested to individual amino acids, only the dipeptides that are inhibited retain a high concentration in the cell. The dipeptides that are not taken up by the brush boarder cells (or are returned undigested) pass on to the large intestine.

3.1.2.5 Necessity of Simultaneous Digestion of Balanced Amino Acids for Protein Synthesis For protein synthesis to proceed within a cell, the full set of amino acids need to be available inside the cell. One way to provide the full set of amino acids is the breakdown (catabolism) of proteins from the host's body itself. This is known to occur all of the time due to protein turnover, but protein catabolism is especially prevalent during fasting and the early phases of starvation. For dietary protein to be effectively utilized in the synthesis of protein from scratch, the full mix of essential amino acids needs to be eaten (and digested) in the same time interval. This is because for most types of amino acids the body does not have a significant storage capacity, other than as protein such as the skeletal muscle (which constitutes a large proportion of the body and is somewhat expendable), and to a lesser extent the proteins of the liver, which are catabolized as well when amino acids are needed by the body.

3.1.3 Some Types of Cells can Uptake Cystine and Efflux Cysteine

Some types of cells (e.g. macrophages, fibroblasts, and hepatocytes) have been found to be able to uptake cystine (CySSCy) via a membrane transport protein and then to reduce it to cysteine (2 CySH) via thiol-disulfide exchange reactions with glutathione (GSH) inside the cell and to subsequently release the cysteine to the extracellular environment (RB170.096:285). Proper function and immune response of lymphocytes requires a local supply of extracellular cysteine (e.g. from adjacent macrophage cells) because when they are stimulated these cells need to be provided with a higher cysteine concentration than that in circulation (AJM91_3C:140S).

The efflux of cysteine from these cells supports the cell-to-cell transport of cysteine (QP552.G58G54:407), which is important because almost all other cell types lack the ability to uptake cystine (CySSCy) and only have the ability to uptake cysteine (CySH). These various types of cells would starve if only provided with cystine (BCHS370:109).

3.1.4 The Intensified Delivery of Cysteine

Because cyst(e)ine is typically the limiting amino acid for most modern diets, insufficient dietary cyst(e)ine is the most likely cause of protein deficiency. Therefore the augmentation of cyst(e)ine delivery can be beneficial in the prevention of its deficiency, perhaps even reducing the amount of total protein that needs to be consumed. For example, if a given mix of dietary proteins is low in cyst(e)ine by 20% relative to the ideal mix of amino acids, significantly more total protein will need to be consumed (25%), just to get enough cyst(e)ine. In an otherwise nutritionally adequate diet, this excess protein, if digested, is likely to end up being converted to body fat.

3.1.4.1 Cysteine Supplementation of Foodstuffs

It would seem that the supplementation of foodstuffs with cysteine would be an effective way to improve the quality of proteins, and this has been done experimentally with soy flour (JN114:2241). But the addition of amino acids to food is regulated by law (and administered by the FDA in the United States). The applicable US law is section 172.320 ("Amino Acids") of Title 21 ("Food Additives Permitted for Direct Addition to Food for Human Consumption"). There are several ways in which this law makes it impractical to use cyst(e)ine as a food additive, as can be seen from consideration of its subsections (c), (d), and (e):

Subsection (c) prohibits the addition of amino acid(s) to any food that is not already a significant source of dietary protein (at least 6.5 grams, based upon 10% of the adult male Recommended Daily Allowance). The added amino acid(s) must result in a statistically significant increase on the Protein Efficiency Ratio (PER) over the naturally occurring protein in the food, and the resulting PER must equal or exceed that of casein (a standard mix of milk proteins). The total amount of cyst(e)ine (additive plus the amount naturally present) cannot exceed 2.3% by weight of the total protein. (This restricts the total cyst(e)ine to less than that of whey protein (2.5%), another type of standard mix of milk proteins.) The applicant notes that this also makes illegal the degree of cysteine supplementation that was utilized experimentally for the improvement of soy flour (2% plus the native cyst(e)ine of soy flour is >2.3%, see section 4.2.2.2 above).

Subsection (d) requires that the PER be measured by AOAC method 43.212-43.216, which involves feeding the protein to rats and measuring their weight gain. (In other words, animal testing is required.) The manufacturer or person needs to repeat these tests sufficiently to "keep and maintain throughout the period of his use of the additive(s) and for a minimum of 3 years thereafter, records of the tests required by this paragraph and other records required to assure compliance with this regulation and shall make such records available on request . . . "

Subsection (e) requires that the label list the name, chemical form, and amount of each amino acid contained in any mixture, and adequate instructions for use (cooking instructions???) to provide a finished food meeting the limitations prescribed by paragraph (c). The record keeping and labeling requirements make it cumbersome to routinely supplement foods with cyst(e)ine, and a brief survey of food labels by the applicant failed to find any that indicated any amino acid supplementation.

It can be seen from these regulations that the addition of amino acids to foodstuffs is (correctly) regarded as potentially hazardous, but the destruction of amino acids (e.g. by anti-microbial radiation) is not. In other words, although food processing procedures that destroy amino acids are commonly designated Generally Recognized As Safe (GRAS) by the FDA, supplementation with amino acids is not. In the opinion of the applicant, supplementation to compensate for the amount of important amino acids that are lost in processing could restore the amino acid balance of the food and would clearly be safe.

3.1.4.2 Prodrugs for Cysteine

Normally, the primary source of cyst(e)ine is dietary protein, but in some cases it is desirable to supply more cyst(e)ine than can reasonably be supplied through the consumption of foodstuffs. Prodrugs for cysteine are compounds that are converted to cysteine via metabolism in the body, some of which can be safely administered in high quantities.

For example, the standard treatment for acetaminophen (Tylenol) poisoning (which causes severe glutathione depletion) is the oral administration of N-acetylcysteine (NAC) (BMCCC6:155). The administered NAC dosage is quite high compared to normal dietary cysteine (an initial dose of 140 mg/kg of body weight (e.g. 9800 mg for a 70 kg person), followed by 17 doses of 70 mg/kg every 4 hours). The low toxicity of NAC, combined with its rapid conversion to cysteine (which in turn is rapidly converted to glutathione inside liver cells) is important for this application.

Cysteine exhibits toxicity in large dosage, but the prodrugs N-acetylcysteine (NAC) and L-2-Oxo-thiazolidine (OTZ) are relatively non-toxic (TL69:15). After enzymatic deacetylization within a cell, NAC becomes normal cysteine (BP23: 1133), Similarly, the intracellular enzyme 5-oxoprolinase converts OTZ to normal cysteine (JSR65:165). Prior to their conversion to cysteine, the reactivity of these prodrugs is lower than that of cysteine because instead of having an exposed "SH" they tend to form a thiazolidine ring in water at a neutral pH (QP801.G6C6, pages 21-30).

When administered chronically (e.g. for the treatment of HIV) NAC can exhibit toxicity. The NAC dosage should be monitored and individually adjusted because excessive cysteine catabolism in the liver can cause toxic ammonia to accumulate, probably due to the inhibition of urea production (JMMED78:55). The dosage in a 7 month long study involving HIV patients ranged from 600 mg/day to 3600 mg/day. The plasma albumin increased approximately 5% with NAC treatment, while the placebo treatment group had a decline of approximately 5%. (Plasma albumin is known to be correlated with plasma cysteine and glutathione.)

Another placebo-controlled trial which was only 8 weeks long administered 8000 mg/day of NAC with no reported toxicity. Whole blood glutathione increased approximately 10% with NAC treatment, while the placebo treatment group had a decline of approximately 3% during the trial period (EJCI30:915).

3.1.5 Cysteine and Cystine Participate in Thiol-Disulfide Exchange Reactions Thiol-disulfide exchange reactions are a unique feature of organosulfur chemistry that provide a rapid, reversible, energy-neutral, highly specific covalent reaction for the bonding together (or the separating) of molecules that incorporate a thiol or a disulfide bond (QP551.T6913:54, QD305.S3C48:633).

The applicant notes that more properly, this type of reaction should have been named the "thiolate-disulfide exchange reaction", because it always involves the ionized version of the thiol (RS⁻). If the disulfide is represented as R'SSR" the exchange is as follows:

In this reaction, the thiolate ion and the disulfide form a temporary complex with three inter-reacting thiyl radicals (RS, R'S and R"S) and an electron, which soon separates with the resulting thiolate ion coming from any of the three thiyl radicals and the remaining disulfide molecule consisting of the other two thiyl radicals.

Thiol-disulfide exchange reactions are a form "redox" reactions, because the R'S group of the disulfide becomes reduced (to a thiolate ion) at the same time that the original thiolate ion (RS⁻) becomes an oxidized group within the new disulfide RSSR". In other words, the original thiolate ion served as a reductant (e.g. antioxidant), becoming oxidized in the process.

It is important to note that because there are a variety of types of reductants and oxidants that can participate in oxidation/reduction reactions (not all of which are thiols or disulfides) there is no single "redox state of a person" or even a "redox state of a cell" but rather there coexist a number of different redox couples, the redox states of which are not necessarily linked to each other (RB170.O96:285).

Researchers have found it useful to define the redox status (REDST) for a set of thiol<->disulfide redox pairs within an environment with its formula being the square of the total thiol concentration divided by the total disulfide concentration. For example, in humans the ratio of total soluble thiol (mainly cysteine) to cystine is approximately ¼ at a young age (e.g. 20-30 years old), but the ratio becomes approximately ⅛ at old age (COCNMC2:227, AEMB543:191). Therefore, the corresponding REDST declines with age by approximately a factor of 4, making this REDST is a useful indicator of the status of physiological aging. Physiological aging has been considered to be a "cysteine deficiency syndrome" that can be prevented or reversed by the use of a cysteine prodrug as a "paravitamin" (PTRSB360:2355).

Like other thiol anions, the ionized form of cysteine ($CyS^-$), will readily participate in thiol-disulfide exchange reactions with disulfides (oxidized thiols), reducing half of the disulfide in the process (QP552.G58G54:73). The resulting oxidized cysteine (either CySSCy or CySSR depending on whether the other reactant contained a cysteinal group) can it turn react with other thiol anions ($R'S^-$) in further exchange reactions, becoming either CySSR' or $CyS^-$ depending on the nature of the other reactant and how they separate.

Of course, this brief description is somewhat of an oversimplification. Exchange reactions can be subject to steric constraints. And the products of the reaction depend on the relative redox potentials of the three thiyl radicals involved (EJB2:327). But in the absence of constraints, the reaction is rapid and the product mix is nearly random (e.g. within a factor of two), resulting in the formation of every possible mixed disulfide (and every possible thiolate ion).

The significant exception to this is when there is stress involved (e.g. if there was a stretching force on the original disulfide). In this case the product mix will tend to be the form which best relieves the stress. Sometimes the stress is compressive. Thiol-disulfide reactions are important in the formation of the cysteine to cysteine bridges within proteins that help determine and stabilize the tertiary structure of the protein (QP552.G58F85:205). They also are involved in the formation of cysteine to cysteine cross-links between proteins.

Many enzymes have an "SH group" at their active site (BIJ63:514), and their activity depends on whether this remains an exposed thiol (PSH), or is an exposed thiolate ion ($PS^-$), or if the thiol is "blocked" by an attached thiyl radical (PSSR). Blocked enzymes are typically less active than unblocked enzymes; although some types of enzymes become more active when they are blocked. This leads to the "redox regulation" of enzymes, which is an important mechanism for regulation, signaling, and control.

Note that the blocking of the enzyme is non-destructive because a new thiol-disulfide exchange reaction between the blocked site and any thiolate ion that happens to float by can result in a disulfide floating away (leaving the SH group on the enzyme as a thiolate ion), thereby activating the enzyme again.

Thiols can also be blocked by other types of redox active molecules such as nitric oxide. In this case, the blocked entity is called a "nitrosothiol" and it can become unblocked via an exchange reaction with a thiolate ion. For example, the activity of the enzyme "nitric oxide synthase" is inactivated by nitrosylation, providing feedback regulation of the level of nitric oxide that it generates (BST23:S136). Note that the degree of feedback regulation depends on the availability of thiolate ions, which reactivate the enzyme via an exchange reaction.

3.2 Glutathione, the Mother of all Antioxidants

Glutathione is a tripeptide composed of the amino acids glutamate, cysteine, and glycine. An advantage of glutathione for the storage and transport of cysteine within the body is that it is far less toxic than cysteine itself, allowing tissues to maintain a high concentration of biothiols in the form of glutathione (QP552.G58G54:57). Due to the available SH group of the cysteine, glutathione is a biothiol and shares the antioxidant properties that are common to thiols. But there are also various enzymes that specifically utilize glutathione, giving it some unique antioxidant and detoxification properties as well.

Glutathione has a high concentration (1-5 mM) in the aqueous environments of most cells and organelles (e.g. in the cytoplasm and inside mitochondria). Glutathione does not pass freely through lipid membranes, but transport systems allow its constituent amino acids to enter cells and also allow GSSG, other glutathione conjugates (GS-X), and in some cases reduced glutathione (GSH) to be excreted from cells or to be transported into organelles such as mitochondria.

Glutathione has a broad diversity of functions in biological systems (too many to do justice to here, see the many examples throughout this application). An extensive treatise on glutathione is available (ARB52:711).

3.2.1 The Antioxidant and Oxidant Properties of Glutathione

Like other thiols, reduced glutathione ($GS^-$, or GSH) will readily donate the electron (or the hydrogen atom) of its SH group, even to relatively weak oxidants. For example, reduced glutathione can react non-enzymatically to reduce $H_2O_2$ and other hydroperoxides, scavenge $*O_2$ (superoxide) radicals, and detoxify other reactive oxygen species (ROS). The conventional view is that this is via electron or hydrogen atom donation, resulting in the formation of the glutathiyl free radical (GS*). Examples of the formation of GS* from the non-enzymatic reduction of a wide variety of ROS are common in the literature (e.g. QD305.S3S14:289). The formation of GS* radicals from a large variety of antioxidant activities of GSH and the fate of these GS* radicals is explored in depth in QP552.G58G566:43. The newly formed free radical is usually a weaker oxidant than the original oxidant and tends to be short lived because it rapidly dimerizes to form oxidized glutathione (GSSG).

Some researchers have concluded that the dimerization of GS* to GSSG can not be by simple conjugation because in normal biological systems the concentration of GS* is always low compared to the concentration of other possible reactants. In other words, before a newly formed GS* can encounter another GS* it will encounter a variety of other molecules that it can readily react with. Given the observed preferential formation of GSSG, the probable reaction paths have been investigated (QP552.G58G566:43, QD305.S3S14:289). In the absence of oxygen, GS* will react readily with the $GS^-$ molecules that are readily available. This conjugation of GS* with $GS^-$ produces $GSSG^{*-}$ which is a powerful reductant. The formation of a powerful reductant from even a mild oxidant has been described as a "molecular switch" that is central to the biological response to oxidative stress. In the presence of oxygen, $GSSG^{*-}$ rapidly reacts with $O_2$ to form superoxide (*$O_2$) and GSSG. Alternatively, the GS* free radical can react directly with $O_2$ to form GSOO* (another free radical). Further reactions of the GSOO* with (for example) GSH produce products such as GSO* and GSOH (a sulfenic acid) along with the formation of GSSG (QD305.S3S14: 289).

The applicant notes that all of these proposed intermediates are significantly more reactive than GSSG itself. The applicant also notes in passing that because GS* has an unpaired electron, it has a magnetic moment and therefore may "diffuse" preferentially in the direction of other GS* radicals. This would lead directly to GSSG formation at a rate significantly faster that would otherwise be calculated on the basis of random diffusion.

In any case, despite some controversy about the path from GSH to GSSG, GSH has been clearly shown to be an effective (and essential) antioxidant in almost all life forms, so the potentially damaging reaction products just discussed must either not form in vivo, or they are effectively managed and have a negligible effect.

Unlike most other thiols, there are a variety of enzymes that are specific to glutathione that augment the antioxidant (and oxidant) activity of glutathione and, indirectly, the other intracellular antioxidants.

Glutathione's antioxidant properties are augmented by various GSH-peroxidase enzymes that use GSH to reduce peroxides (e.g. hydrogen peroxide), producing GSSG in the process, which in turn is reduced back to 2 GSH by GSH-reductase (ARB52:711). Glutathione transferases (see below) also have peroxidase activity.

Glutathione (GSH) serves as a critical antioxidant and is perhaps the only molecular antioxidant whose total depletion can directly cause death (RB170.096:101). The central antioxidant role of glutathione is due to its ability, via the "antioxidant network" (QP772.A8:139, FIG. 9.2), to recycle almost all other antioxidants to their reduced state. Therefore, insufficient GSH can also result in the accumulated oxidation of the various other antioxidants.

Glutathione has two major roles in the antioxidant network (See FIG. 1, derived from FIG. 9.2 of QP722.A8A586:133), the first of which is illustrated by a sequence of oxidation/reduction reactions originating with a pre-existing oxidized molecule within the lipid membrane (R*). This molecule can oxidize vitamin E, becoming reduced in the process. The newly oxidized vitamin E (tocopheroxyl radical) is less reactive than the original oxidant. The oxidized vitamin E may then oxidize an ascorbate molecule (vitamin C), becoming reduced in the process. The oxidized vitamin C (ascorbyl radical) can in turn oxidize a GSH molecule, becoming a reduced (ascorbate) molecule again (FRBM20:543). The oxidized GSH molecule (GS*) is rapidly dimerized to GSSG. Hence the original oxidant has caused the formation of a relatively non-reactive GSSG molecule, with vitamins E and C being used (and recycled) in the process. This series of reactions can proceed non-enzymatically, although there are also enzymes available which can accelerate some of the steps (e.g. thiol transferases).

The second major role is more specific to glutathione. The GSSG that has been produced can in turn be recycled to 2 GSH by the enzyme glutathione reductase. This enzyme uses NADPH+$H^+$ as a reductant, producing $NADP^+$ which is typically recycled back to NADPH as part of the pentose pathway of energy metabolism. Various other antioxidants can serve as intermediates in an oxidation/reduction pathway, still leading to the formation of oxidized glutathione (GSSG) and its ultimate reduction by NADPH. The net effect is that the energy input (e.g. from glucose) drives the reduction of GSSG, which in turn drives the reduction of the other antioxidants that participate in the antioxidant network. Therefore, glutathione serves as a critical link between the "non-enzymatic" antioxidants and the cellular energetics which ultimately drives the system. (Vitamin C can serve a similar role, because there are specific enzymes that utilize NADPH for its reduction too.)

Interestingly, vitamin C has been shown to be able to pass through the cellular membrane of red blood cells and to thereby couple the intracellular antioxidant network to the external environment (JCI63:53). The uptake of oxidized vitamin C (DHA) is active via the glucose transporter in the cell membrane and can operate against a concentration gradient, while the reduced vitamin C (ascorbate) diffuses from the cell through the cell membrane back to the extracellular environment (FRBM24:789). The capacity for this "ascorbate cycling" by red blood cells is substantial (plasma vitamin C can be completely recycled in 3 minutes). The recycled ascorbate also protects the vitamin E in LDL from oxidizing (FRBM24:789).

Another example of the ability of the glutathione reductase driven antioxidant system to convert disulfides to thiols is illustrated in FIG. 2. In this illustration the compound SAMC (consisting of the mixed disulfide between allyl mercaptan and cysteine) is taken into the cell by a transmembrane transport protein. Within the cell, the SAMC is exposed to a large concentration of glutathione, approximately 3% of which is in the form of the reduced anion ($GS^-$) which will readily participate in a thiol-disulfide exchange reaction. The resulting products depend on how the reaction complex splits up, producing either $AS^-$+CySSG or $CyS^-$+ASSG. Further exchange reactions with the $GS^-$ ions eventually produce an oxidized glutathione molecule (GSSG) which is then rapidly reduced to 2 GSH by glutathione reductase. This produces a net decrease in the total disulfide concentration and a net increase in the total thiol concentration (which up to now have remained constant). Over time, the combination of random exchange reactions and the action of glutathione reductase will drive the disulfide concentration down to almost zero (e.g. 3%) and the net products from the original SAMC will be the thiols allyl mercaptan and cysteine (US2005/0260250A1).

The cell maintains a low concentration of glutathione disulfide (GSSG), the oxidant properties of which are augmented by the enzyme Protein Disulfide Isomerase (PDI), which accelerates the formation of intramolecular disulfide bonds, using GSSG as the proximate oxidant (QP552.G58F585:125). Other essential oxidant properties of glutathione include its redox regulatory roles, including the control of proteins and enzymes via glutathonylation (the S-thiolation of exposed thiols on proteins) (BBRC242:1).

The concentration of glutathione disulfide (GSSG) is typically ~3% of the concentration of reduced glutathione (GSH) within a cell. The applicant notes in passing that he has observed in the published experimental results of others (for example in Table 2 of AJPEM275:E359) that if a cell becomes glutathione depleted (i.e. the intracellular total glutathione concentration declines), the GSSG concentration tends to remain relatively constant, implying that the GSSG concentration is independently regulated within cells.

3.2.2 The Detoxification Properties of Glutathione

Glutathione is also necessary for the detoxification of a wide variety of toxic substances (ARB52:711), including pesticides, herbicides, pollutants, and industrial solvents. As a biothiol, it shares the various detoxification properties of biothiols, including the formation of complexes with metals that would otherwise be more toxic (e.g. mercury, the ability of which to be captured by thiols was observed by the alchemists, hence the name "mercaptan" for various thiols). But there are also various glutathione specific enzymes, especially the glutathione transferases, which greatly enhance the detoxification properties of glutathione.

3.2.2.1 Glutathione Transferases

The GSH-transferase enzymes (GST) bind various substances (especially those that are electrophilic) to glutathione molecules, which are then excreted from the cell (and ultimately from the body). In some instances an electrophilic center was previously created on the molecule by another reaction, such as those catalyzed by the cytochrome P-450 "phase I detoxification" enzymes. The subsequent conjugation of the now electrophilic molecule to glutathione is "phase II" of the detoxification system.

The resulting conjugate may also be toxic, but it is typically more readily excreted than the original molecule. This is especially the case for hydrophobic compounds (which could otherwise accumulate in the membranes of cells) because the conjugates, being water soluble, are more easily transported to the liver and kidneys by the circulatory system.

There are various GST enzymes which vary in their preferred substrates, although each GST typically will have low substrate specificity and therefore their substrate ranges can overlap. The GST enzymes are induced as necessary. In practice, this means that the prior exposure to a low level of a toxin will induce the production of the appropriate GST and the tolerance for a repeated exposure to that toxin will be increased. Because of the broad specificity of GSTs, this will also provide protection from other (sometimes seemingly unrelated) compounds. For example, various organosulfur compounds from garlic and onions have been shown to increase GST activity sufficiently to provide protection from the carcinogen benzo[a]pyrene, reducing the tumor incidence in mice to as low as 14% of the control (CG9:131).

Glutathione is also a required coenzyme for other detoxification processes. For example, insufficient GSH (e.g. from depletion due to alcohol consumption) is responsible for acetaminophen (Tylenol) toxicity, which is the second largest class of toxic drug ingestions in the United States (BMCCC6: 155).

Because exposure to toxins is normally rare, people with glutathione deficiency can seem well nourished and healthy (until they are exposed to a toxic substance). However, some populations are continuously exposed to toxins, resulting in chronic health problems if there is concurrent glutathione deficiency. For example, in regions where the drinking water is arsenic contaminated, toxicity has been shown to correlate positively with low consumption of animal protein (EHP112: 1104). Animal protein is typically the most significant dietary source for cyst(e)ine (the limiting amino acid for glutathione synthesis) so these people are more likely to be glutathione deficient. In other words, even though these people will typically develop a high expression of the arsenic detoxification enzymes, these enzymes will be ineffective due to the lack of a required cofactor (glutathione).

3.2.2.2 The GS-X Pump Excretes Glutathione Conjugates from Cells

Cell membranes use a special transport system (the "GS-X pump", also known as "MRP" multidrug resistance proteins, of which there are several types in humans) that can excrete via exocytosis (QP606.G59G59:199) any glutathione conjugate with a molecular weight over ~350 (GSH itself has an MW of 307). This constitutes the "phase III" of the detoxification system. Glutathione chelate complexes of metals (e.g. arsenic) are also excreted by the GS-X pump. The GS-X pump has been extensively studied due to its role in the detoxification of various anti-tumor chemoraputic drugs, such as Cisplatin, thereby reducing their effectiveness (QP606.G59G59:199). Tumor cells with increased expression of the GS-X pump are termed "multidrug resistant".

The GS-X pumps are members of the "ATP-Binding Cassette" (ABC) class of membrane transport proteins that include hundreds of members that selectively transport small molecules in or out of cells, organelles, vesicles, and microsomes. Typically, the ABC transport proteins have two bundles of six alpha helices each, connected by a flexible domain that includes an ATP binding site and terminating in a second domain that includes a second ATP binding site. However, it is not clear how the glutathione conjugates are selectively passed through the GS-X pump, both because of their variability and because of their relatively large size.

Experiments utilizing a fluorescent glutathione conjugate molecule (GSH-bimane) have shown via microphotography that the glutathione conjugates can accumulate within intracellular vesicles that then move to the plasma membrane and fuse to the plasma membrane (QP606.G59.G59:199). This exocytosis results in the contents of the vesicle being released to the outside of the cell and the GS-X transport proteins that were in the vesicle membrane becoming part of the cell's plasma membrane. Therefore, the GS-X pumps are thought to both directly pump the glutathione conjugates through the cell's plasma membrane and to also pump the glutathione conjugates into intracellular vesicles (QP606.G59.G59:199).

3.2.3 The Role of Glutathione in Signaling and Control

Glutathione has a variety of roles in signaling and control, the most important of which may be its ability to "block" the SH groups that determine the function and activity of many types of proteins and enzymes. This is called "glutathionylation", and the applicant notes that this occurs to a significant degree inside cells.

Glutathione is a major participant in the oxidant-mediated regulation of cellular division (mitogenesis) and both apoptotic and necrotic cell death (BBRC242:1). Small amounts of oxidative stress are seen to promote cellular division, while larger amounts of oxidative stress can induce apoptosis (EJ-CELLB68:47), a form of programmed cell death in which the cell, in effect, disassembles itself into non-toxic fragments. Prior to and during apoptosis there is significant loss of glutathione from the cell, yet a minimum amount of glutathione preservation appears to be necessary for the cell to avoid necrotic cell death (which produces an uncontrolled release of cellular contents (such as DNA) that can provoke a strong immune response and be damaging to the host).

Glutathione has been found to be necessary for the proper recruitment of neutrophils to the site of infection during sepsis. Treatment with the GSH precursor N-acetylcysteine both potentiates the host defense and limits the inflammationary damage to the host (JID185:1115).

3.2.4 Variability in Glutathione Levels

Various factors have been found to modify the localization and concentration of glutathione within organisms.

3.2.4.1 Dietary Sources of Glutathione

Glutathione in food varies dramatically, such that well fed Americans can have a 40:1 range in its consumption (JFCA2: 327). However, dietary glutathione probably has no special significance other than as a source of cyst(e)ine. The glutathione inside cells is created from its constituent amino acids (glutamate, cysteine, and glycine). Of these, cysteine is almost always the limiting amino acid, because glutamate and glycine are relatively common in foods. The extracellular glutathione (e.g. in the blood plasma) typically has been excreted from cells, not directly absorbed during the digestion food.

Some dietary ingredients have been shown to augment glutathione. For example, dietary garlic or onion powder has been shown to increase the liver glutathione level in chickens by 40% (RM666.G15K6313, page 190). Consumption of garlic produces an increase in the reduced glutathione level, which was attributed to its increasing the activity of the GSH reductase enzyme by up to 87% (RM666.G15K6313, page 190), thereby increasing the proportion of GSH to GSSG. The administration of SAMC has been shown to significantly increase the total glutathione level of cells (CR61:725), which was attributed to the induction of the GSH synthesis enzymes.

3.2.4.2 Unbalanced or Excessive Vitamin Consumption

Although vitamin C and glutathione in many ways work together and vitamin C can partially substitute for glutathione as an antioxidant, excessive vitamin C consumption has been shown to significantly decrease the glutathione content of cells. This effect has been utilized in a clinical trial where the goal was to increase the cytotoxicity of the chemotherapeutic drug arsenic trioxide (which is normally detoxified by glutathione within cells) against the cancer multiple myeloma (CCR8:3658). A daily dosage of 1000 mg of vitamin C caused significant glutathione depletion, resulting in a mean percentage decrease of 60% among the patients.

Vitamin A and other carotenoids can also cause depletion of glutathione and other thiols. The main antioxidant property of the carotenoids is the quenching of singlet oxygen, with each carotenoid molecule able to do this approximately 1000 times before it breaks down and forms a very reactive aldehyde molecule. These break down products form adducts with SH groups that are not reversible. Carotenoid breakdown products are otherwise long lived and can travel far before they encounter (for example) an SH sensitive enzyme, producing a cumulative inhibition of SH enzymes in the body. Carotenoid levels, especially beta-carotene in blood and various tissues are dependent on the carotenoid content of food and may exceed the levels that were used in these enzyme inhibition studies (RB170.H36:235).

The applicant notes that this apparently little-known toxicity of carotenoids may explain the poor results from the "beta-Carotene and Retinol Efficacy Trial", which showed that carotenoid supplementation significantly increases cancer risk and overall mortality (CBEP12:350). A detailed post-analysis revealed that the carotenoid consumption of the people in the "intervention arm" of the placebo controlled trial completely eliminated the beneficial effects of fruit and vegetable consumption. Only the people in the "placebo arm" of showed a lowered cancer risk related to fruit and vegetable consumption. Interestingly, Table 2 of this report shows that high "Total fruits" consumption resulted in a lower relative risk factor (0.56) than that of any individual category of fruits (which had a range of 0.63-0.73).

In the opinion of the applicant, this indicates either that a broad mix of fruits is necessary, or that there is some "magic bullet" fruit that is included in the "total fruit" category but not in the more specific sub-categories. The applicant notes that the high consumption of vegetables in the report's "Other vegetables" category (which includes onions and presumably garlic) resulted in a lower relative risk factor (0.56) than that of "Total vegetables" (0.82). Among the types of vegetables that were separately categorized, the Cruciferae (which are a good source of organosulfur compounds) produced the lowest relative risk factor (0.68) than that of any other individual category of vegetables (which had a range of 0.80 to 1.38) (CBEP12:350).

3.2.4.3 Glutathione Synthesis

Glutathione is synthesized in two stages. First the enzyme gamma-glutamyl-cysteine synthase combines glutamate with cysteine (producing a gamma-glutamyl linkage instead of the peptide linkage that is used for other dipeptides). The resulting molecule of gamma-glutamyl-cysteine is then combined with glycine by the enzyme glutathione synthase to produce the molecule of glutathione (QP514.M45:101).

Each of these steps utilizes a molecule of ATP for energy and therefore two molecules of ATP are consumed. Interestingly, both steps are reversible, indicating that the breakdown of glutathione back to its constituent amino acids can convert 2 ADP to 2 ATP in the process (QP514.M45:101). The applicant notes that the glutathione pool therefore constitutes a stored form of energy, which is available for ATP synthesis when other sources of ATP become depleted.

The rate of glutathione synthesis is generally considered to be limited by the first step, either due to low availability of cysteine or due to feedback inhibition based on the level of glutathione (GSH) (QP514.M45:101). This enzyme actually has its activity lowered by GSH and increased by GSSG (the opposite of mote SH sensitive enzymes), suggesting that there is an exposed SH group that must be blocked for higher enzyme activity.

After loss of glutathione due to the trauma of surgery (AJPEM275:E359), the rate of the second step (glutathione synthase) can be limiting, and the low glutathione level in skeletal muscle can persist for a long time. In this case, the reduced rate of glutathione synthesis appears to be due to a 40% drop in glutamate, because the concentration of cysteine remained unaltered postoperatively.

3.2.4.3.1 The Augmentation of Glutathione 3.2.4.3.1.1 Cysteine Prodrugs can Increase Glutathione In the case where cyst(e)ine availability is limiting, augmentation of the cyst(e)ine level will allow the increased synthesis of glutathione. Several methods for this were presented in section 4.2.4.2.

SAMC is another compound that has been studied as a means to deliver cyst(e)ine and increase glutathione levels. In vitro experiments show that when cells are administered SAMC (which contains a cysteinyl radical that can easily be converted to cysteine in vivo, e.g. by a thiol-disulfide exchange reaction with a thiolate ion. The result is a significant increases the total glutathione level of cells (CR61:725).

The glucose-cysteine adduct formed by the glycation of cysteine (Glc-cys) has been shown experimentally to prevent the GSH decline normally observed in perfused liver (e.g. livers destined for transplantation), and has also been shown to be the most effective (among 8 cysteine prodrugs tested) in raising the GSH level in heapatocytes that were exposed to acetaminophen (AACID12:33).

It is also observed that glycated cysteine (D-glucose-L-cysteine, DGC) forms within infant formulas that are supplemented with cysteine, raising the question of the bioavailability of cysteine in these infant formulas. In vivo experiments were performed utilizing mice to determine if DGC can provide bioavailable cysteine (TOXL70:101). The hepatic injury from acetaminophen administration was significantly reduced if the DGC was administered 4 hours previously, but DGC was not effective if it was administered simultaneously, indicating that DGC can serve as a cysteine prodrug but it is not a good cysteine prodrug to use when rapid resupply is needed. Also, the significant excretion of DGC in urine indicates that the cysteine administered as DGC is not fully bioavailable.

3.2.4.3.1.2 Compounds that Bypass Gamma-glutamyl-cysteine Synthase

Because the first step in glutathione synthesis is usually the limiting one (either due to cysteine availability or due to feedback inhibition of the enzyme), bypassing this step through the administration of gamma-glutamyl-cysteine or a prodrug for this compound can raise the glutathione level beyond that which would be normally present in the cell. The administration of the compound gamma-glutamylcysteinyl-ethyl ester has been found to be an effective, non-toxic way to do this (BBA1313:47).

3.2.4.3.1.3 Whey Protein

A particularly good source of cyst(e)ine is whey protein, which is sold as a dietary supplement. Whey Protein consumption has been shown to increase glutathione levels, with a wide variety of associated health benefits. It has also been claimed that the undenatured cystine in whey protein is more bioavailable than other dietary sources of cyst(e)ine (US005451412A).

While whey protein is an excellent source of cyst(e)ine, its bioavailable cyst(e)ine is reported to be very sensitive to denaturation from heat or mechanical shock, requiring a microfiltration process to be used during its manufacture. If not prevented, this denaturation causes a significant decrease in the ability of whey protein to raise the glutathione level of the host. Even the transport by un-refrigerated truck can possibly cause this damage (US005451412A).

3.2.4.3.1.4 Pharmaceutical Preparations of Glutathione

A method for increasing glutathione levels in mammals has been developed which utilizes encapsulated pharmaceutically stabilized glutathione in a rapidly dissolving formulation (US006896899B2).

3.2.4.4 Glutathione Depletion

3.2.4.4.1 Glutathione Synthesis Inhibitors

The glutathione level within cells can be intentionally lowered through the use inhibitors of its synthesis, such as BSO (Blood 93:268). This can be useful in experiments, for example to demonstrate that some cellular process is glutathione dependent. The depletion of glutathione also has clinical application as a means to increase the cellular toxicity of chemotherapeutic agents in the treatment of cancer.

3.2.4.4.1.1 Extreme Glutathione Depletion Kills Animals (and Cells)

Experimentally, by inhibiting glutathione synthesis, it has been shown that glutathione depleted animals die within a few days. Some types of cancer cells are naturally low in glutathione and can be selectively killed by further lowering their glutathione level.

3.2.4.4.2 Glutathione Reductase Inhibitors

Glutathione reductase inhibitors are also useful experimentally to alter the GSH/GSSG ratio, for example to demonstrate that some cellular process is thiol/disulfide redox sensitive.

3.2.4.4.3 Lifestyle Choices

Activities such as smoking, drinking alcohol, and excessive exercise cause glutathione depletion. Improperly balanced vegetarian or other "healthy" diets can result in a low glutathione level if an inadequate amount sulfur amino acids are being consumed.

3.2.4.4.4 Glutathione Excretion

The formation (and elimination) of glutathione conjugates (GS-X) leads to their excretion from the cell (QP606.G59G59:199), which can deplete cellular glutathione in the process. The glutathione conjugates can either be produced by the glutathione transferase proteins (GSTs) or by normal oxidation of GSH to GSSG (its antioxidant function), especially in situations where glutathione reductase has been inhibited.

The applicant notes that persons that are exposed chronically to a glutathione depleting agent (e.g. arsenic) require increased protein consumption in order to maintain a healthy level of glutathione.

3.2.4.4.4.1 Depletion due to Acetaminophen can be Fatal

The second largest cause of drug-induced death in the US is the ingestion of acetaminophen (e.g. Tylenol). Even the recommended dosage can be fatal to people whose glutathione level is low, such as alcoholics (BMCCC6:155). The depletion is due to the metabolism of the drug, which produces a glutathione conjugate that is excreted from cells. This can cause fatal liver damage if the liver cell glutathione level becomes overly depleted.

3.2.5 Mysterious Changes in the Level of Cysteine and Glutathione

Some of the increases, decreases, and fluctuations of the cyst(e)ine and glutathione levels in the body are not fully understood.

3.2.5.1 Age Related Decline in Cysteine and Glutathione

An assay of the plasma concentrations of GSH and GSSG in the plasma of ~300 Chinese volunteers aged from 21 to 61+ shows significant decline with age in the GSH concentration (from 1.1 down to 0.5 micromoles), along with a relatively constant level of 2 micromoles for the GSSG concentration (increasing ~10% with age). Therefore, the ratio of GSH/GSSG declined to ~40% of the initial level with increasing age (JCHROMB674:23). The reason for this is not understood but it may be related to the increase in plasma glutamate level that is simultaneously observed (BLOOD92:59), because glutamate competitively inhibits the uptake of cystine by fibroblasts.

A variety of measurable characteristics associated with physiological old age have been shown to be mutually correlated, including the plasma thiol/disulfide redox state, the intracellular thiol/disulfide redox state, the plasma albumin level, and loss of body mass (EG37:1331). The administration of N-acetylcysteine has been proposed as a method to prevent or reverse these changes, for example to readjust the plasma thiol/disulfide REDST to the level expected of a young healthy individual, however it is recommended that the patient be monitored at suitable time intervals and the dosage should be adjusted to the individual (EG37:1331).

3.2.5.2 Daily Cycle of Liver Glutathione Content

The glutathione content of the liver rises and drops each day, being highest in the morning and lowest in the afternoon.

3.2.5.3 Glutathione Loss During Exercise

During exercise the glutathione level of the liver declines, perhaps indicating a net flow of glutathione from the liver to muscle cells. The cause of the glutathione loss in the liver is not understood, but is can be partially prevented by pretreatment with a cysteine prodrug, such as milk protein and/or N-acetylcysteine (JN134:128).

4. SUMMARY OF THE INVENTION

The published art techniques for augmenting cysteine in the body typically involve either the administration of some form of highly digestible cyst(e)ine (e.g. whey protein) or the administration of a prodrug for cysteine (e.g. N-acetylcysteine). The applicant has determined that the effectiveness of these methods is limited by the rapid extracellular formation of cysteine disulfide (cystine) from the cysteine or the cysteine prodrug that was administered. This loss of effectiveness is because the cystine that is formed is less bioavailable than cysteine itself.

In order to have high bioavailability, the cyst(e)ine must be available where and when needed within the body in a form which can be readily utilized for biological or biochemical purposes. The bioavailability is poor if it is not available where it is needed, or if it is in a form that can not be readily utilized, even if it is available in other locations or in other forms within the body.

Although some types of cells (e.g. macrophages, fibroblasts, and hepatocytes) are able to take up cystine and are therefore well nourished in a high cystine environment, many other types of cells in the body are only capable of taking up cysteine and therefore can become "cysteine starved" if there is an insufficient amount of cysteine in circulation. Because the plasma concentration of cystine significantly exceeds the plasma concentration of cysteine (e.g. 6 to 1) the net bioavailability of cyst(e)ine depends primarily on the concentration and distribution of cysteine.

The published art techniques for the augmentation of cysteine also produce a significant increase in the concentration of cystine. For example, N-acetylcysteine (NAC) is commonly administered either as a cysteine prodrug or as an antioxidant, but soon after each NAC molecule is de-acetylated to form cysteine it is likely to become oxidized to cystine and is no longer available as part of the cysteine (or antioxidant) pool. Because the cysteine in plasma is being continually oxidized to cystine, the dosage required to keep the cysteine concentration elevated throughout the day is high (e.g. 1000-8000 mg), which significantly exceeds the normal daily amount of dietary cyst(e)ine (e.g. 900 mg). The net accumulation of cystine shifts the plasma REDST, thus the excessive oxidation of cysteine in the blood must be prevented (EG37:1331). This limits the utility of NAC treatment outside of a clinical environment. The NAC dosage should be monitored and individually adjusted because excessive cyst(e)ine catabolism in the liver can cause toxic ammonia to accumulate, probably due to the inhibition of urea production (JMMED78:55).

The applicant has discovered a method to improve the bioavailability of cysteine, even in the case where the total amount of cyst(e)ine in the body remains constant. This facilitates the delivery of cysteine into cells throughout the body, which also augments the intracellular formation, storage and utilization of glutathione. The total amount of cyst(e)ine available is typically limited by the diet, perhaps even dietary deficiency. However, even in this case, by converting extracellular cystine to extracellular cysteine, the amount of cysteine in circulation is increased and cellular nutrition is improved.

The applicant has discovered that there is a class of compounds which metabolize to membrane permeable thiols that can serve as an extracellular antioxidant, becoming oxidized to form membrane permeable disulfides. Furthermore, after their extracellular formation, the membrane permeable disulfides can eventually diffuse into cells and be reduced to re-form the original membrane permeable thiol. The applicant had further discovered that the cycling between the thiol and disulfide states gives these membrane permeable compounds important antioxidant and anti-inflammatory properties, including the ability to serve as an extracellular antioxidant that is coupled to the intracellular glutathione reductase system. This recycling also increases the effectiveness of even a low concentration of these compounds. The co-pending patent application (US2005/0260250A1) presents experimental evidence from in vitro experiments with red blood cells that show the intracellular formation and extracellular availability of a membrane permeable thiol and a membrane permeable disulfide.

In vivo experiments have been performed and are reported herein that show that the administration these compounds to a human at a moderate dosage (e.g. 30 mg/day) produces a significant increase in the ratio of cysteine/cystine in blood plasma.

A wide variety of diseases and conditions are known to either be caused by, or to be aggravated by, or to cause cysteine depletion. The diseases that cause cysteine depletion can in turn aggravate (or even cause) other diseases that are related to cysteine depletion. One such disease is shown to be chronic arsenicosis, and its mitigation by the oral administration of these compounds has now been shown in a small scale clinical trial. Other such diseases and conditions include AIDS, diabetes, cancer, sub-optimal immune function, sub-optimal body weight, and physiological old age.

The compounds associated with the present invention are suitable for administration in nutraceutical, dietary supplement, and drug formulations and methods for producing and administering such formulations are taught in the co-pending patent application US2005/0260250A1 by the present applicant. When administered in either nutraceutical form or as a dietary supplement, general health benefits are provided while offering some protection from various potential diseases. A higher dosage can be utilized when increased protection is desired, for example, in the event travel that could involve exposure to infectious diseases, or during low-level exposure to an environmental toxin, or for the treatment of a chronic disease. A still higher dosage can be used as a drug for acute or catastrophic care during the treatment of a disease.

Particular embodiments are disclosed that are "low tech" in that they utilize inexpensive ingredients and a simple manufacturing process, allowing their widespread manufacture and use by economically disadvantaged groups.

Other aspects, advantages, and novel features of the invention are described below or will be readily apparent to those skilled in the art from the following specifications and drawings of illustrative embodiments.

5. BRIEF DESCRIPTION OF THE DRAWINGS

Figure 1:
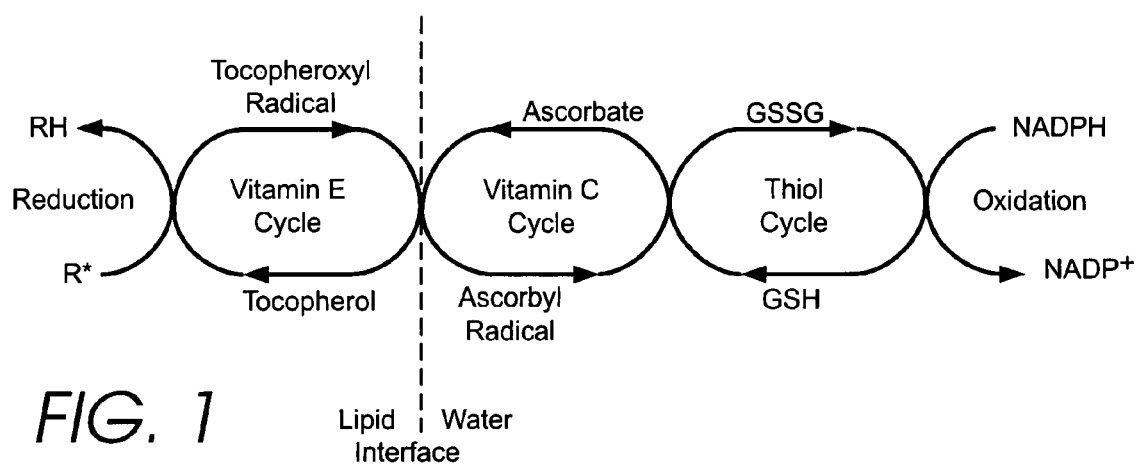
FIG. 1 is a diagram illustrating the participation of glutathione in the thiol cycle of the antioxidant network.

6. DETAILED DESCRIPTION OF ILLUSTRATIVE EMBODIMENTS 6.1 Augmentation of Cysteine and Glutathione Although other researchers who have studied the disease or age related change in plasma thiol/disulfide REDST have attempted to modify it through the use of cysteine prodrugs, the applicant has discovered that their approach inevitably increases the level of cystine and is therefore inherently somewhat self-defeating. Although cysteine supplementation can clearly be beneficial when there is an actual cyst(e)ine deficiency, in many cases sufficient cyst(e)ine is present but the REDST problem is that too much of it is in the form of cystine.

The applicant has discovered that in many cases it is more appropriate to reduce the existing cystine to cysteine, and that an extracellular antioxidant can be utilized to do this. The applicant has further discovered that a membrane permeable thiol that oxidizes to form a membrane permeable disulfide can function as a recycling transmembrane redox shuttle, effectively coupling the reductive intracellular antioxidant network to the extracellular environment, thereby serving as a potent extracellular antioxidant.

6.1.1 Conversion of Extracellular Cystine to Cysteine

The applicant has determined that the thiol compound allyl mercaptan (AllylSH) is membrane permeable and that its oxidation product diallyl disulfide (DADS) is also membrane permeable. Both of these compounds are also classified "Generally Recognized as Safe" for use as a food additive for flavoring purposes by the FDA. They are also both metabolites of digested alliums (e.g. garlic) which have been safely consumed by large populations for thousands of years. Therefore they were chosen to serve as model compounds for the research described below. Furthermore, S-AllylMercapto-Cysteine (SAMC) was chosen (instead of AllylSH) for use as the starting ingredient because this more conveniently allows the formation and localization of AllylSH and DADS to be assayed.

6.1.1.1 Criteria for Membrane Permeability

It is desirable for the compound to be sufficiently water soluble to be distributed by the blood stream, and this criteria is met by AllylSH, DADS, and SAMC. In order to pass through a cellular membrane (a hydrophobic, lipid environment) the compound must also be sufficiently lipid soluble to enter the membrane and pass though it.

A convenient measure of the relative ability of a compound to be water and/or lipid soluble in this context is its partition coefficient. To measure the partition coefficient of a compound between two solvents (e.g. between water and a representative hydrophobic liquid) both solvents are put into a container, the compound to be tested is added, everything is mixed thoroughly, and then the relative concentration between the two solvents of the test compound is assayed. The partition coefficient DADS has previously been determined to be 25.0 for n-octanol/water (JAFC50:6143). Although no published partition coefficient for allyl mercaptan was found, the partition coefficients were in the range of 0.3 to 0.4 for the other small non-polar molecular thiols reported in JAFC50:6143. The value 0.4 will be considered here to be a lower limit for the partition coefficient for AllylSH because it is reported in the Flavoring Agents Database of the Joint FAO/WHO Expert Committee on Food Additives to be more soluble in alcohol than it is in water. For comparison, the partition coefficient for alpha-tocopherol (vitamin E, which is concentrated in lipids, QP722.A8A586: 133) is 550 (JAFC50:6143).

It will now be shown that a compound can diffuse through a cellular membrane reasonably quickly if its partition coefficient is within the range of 0.1 and 100. The reason for this is that the membrane is very thin compared to the volume of aqueous cytosol inside the cell. Therefore the volume of lipid material in the membrane is also small compared to the volume of the cytosol (for example, 1% of the total volume of the cell). Clearly, if the relative steady state concentration of the compound in the lipid membrane is 0.1, a moderate amount of the compound will be able to enter the membrane, but it won't tend to stay in the membrane for long. Given that the membrane is thin, a reasonable percentage of the compound that enters the membrane can reach the center of the membrane and then with equal probability will exit it on either side of the membrane. Therefore, the concentration of the compound can equilibrate reasonably quickly (e.g. within milliseconds) on both sides of a thin membrane.

For a compound which is more lipophilic, with a partition coefficient of, for example, 99, it will quickly enter the membrane and reach a high concentration there. But given that the membrane is only 1% of the total volume, half of the compound will still partition into the aqueous environment within the cell. (If 1% of the volume (lipid) has 50% of the compound, and the other 99% of the volume (cytosol) has 50% of the compound, the concentration in the cytosol will be 1/99 that of the lipid, which is the equilibrium point indicated by the given partition coefficient in this example.)

These examples indicate that if the partition coefficient is low the compound will enter the lipid slowly but then will exit it quickly, or if the partition coefficient is high, the compound will enter the lipid quickly, "fill it up" and then overflow into the other side until the concentrations on both sides equilibrate. Therefore, if the partition coefficient for the compound is within the range of 0.1 to 100 it can equilibrate on both sides of the membrane reasonable quickly.

The partition coefficient for DADS is 25 and the lower bound for the partition coefficient for allyl mercaptan is estimated as 0.4, so each of these is well within the range illustrated by these examples. The specified range of 0.1 to 100 extends to 4× above the value for DADS and down to ¼ the estimated value for allyl mercaptan, so any other compounds within this range can reasonably be expected to perform acceptably well in comparison with the experimental results presented below.

In contrast, the other cysteine prodrugs that have been used by researchers (such as N-acetylcysteine) are not membrane permeable to any significant degree at all because they are amino acids (which have polar carboxyl and amino groups) or are otherwise too polar to diffuse through the cellular membrane.

6.1.2 Demonstration of Extracellular Antioxidant Formation

Figure 2:
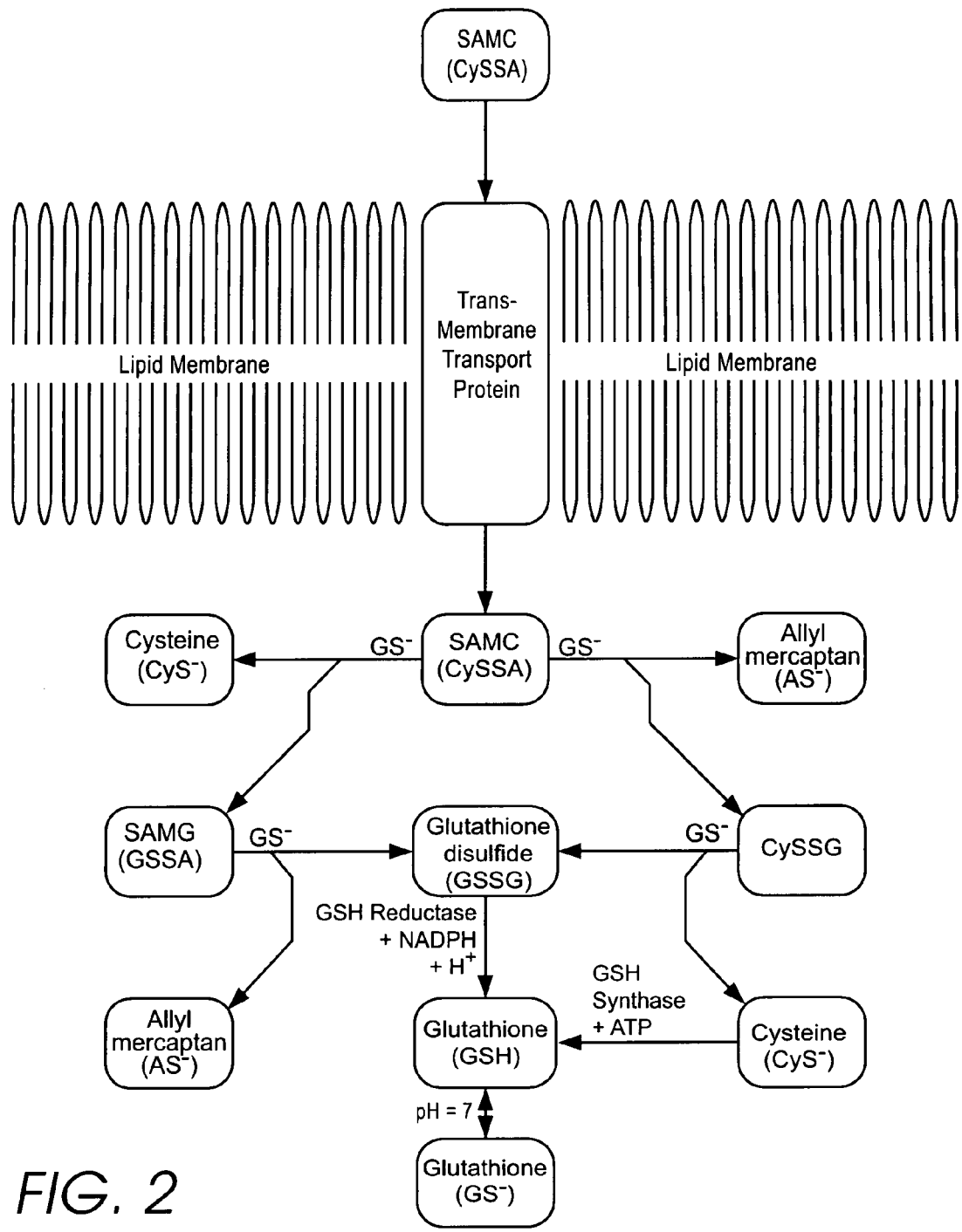
FIG. 2 is a diagram illustrating the cellular metabolism of SAMC and some of the thiol-disulfide exchange reactions involved.
Figure 5:
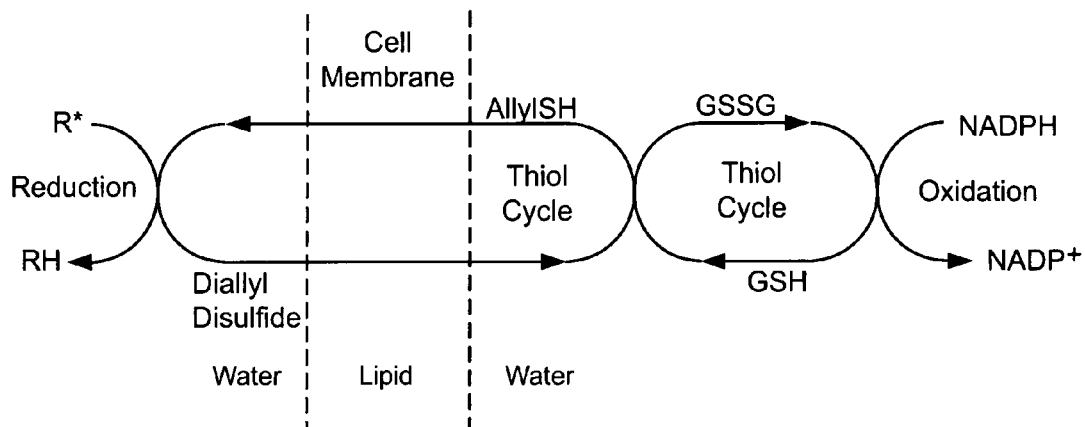
FIG. 5 is a diagram illustrating the transmembrane coupling of an extracellular antioxidant with the intracellular antioxidant network.

The following experiments show that SAMC can be taken-up by cells, converted to allyl mercaptan and cysteine inside the cell (as illustrated in FIG. 2), and then the allyl mercaptan can leave the cell to serve as an extracellular antioxidant (as illustrated in FIG. 5) capable of converting cystine to cysteine via normal thiol-disulfide exchange reactions.

6.1.2.1 The Intracellular Formation of Allyl Mercaptan, Cysteine, Etc.

For these experiments, 0.25 ml of packed RBCs were suspended in 1.75 ml of phosphate buffer solution (PBS) along with an initial concentration 0.5 mM of SAMC.

FIG. 2 illustrates the anticipated metabolic pathway of a low concentration of SAMC administered to red blood cells (RBCs), concentrating on the most significant thiol-disulfide exchange reactions (those involving GSH, the highest concentration thiol in the cell). Even this simple system involves three types of thiols (and their anions) and will also tend to have three types of mixed disulfides and three types of homogeneous disulfides present. The thiols present are Cysteine (CySH, CyS$^-$), reduced glutathione (GSH, GS$^-$) and allyl mercaptan (ASH, AS$^-$). The mixed disulfides are CySSA, CYSSG, and GSSA.

For simplicity, the intracellular formation of the disulfides CySSCy (cystine) and ASSA (diallyl disulfide, normally abbreviated as DADS) are not shown in FIG. 2, which can be justified if the incoming concentration of SAMC is low. This figure also only shows the exchange reactions involving glutathione as the thiol, because the intent is to illustrate the involvement of glutathione (the highest concentration intracellular thiol) and its associated enzymes in the production of AllylSH and cysteine (CySH) from SAMC.

The thiol-disulfide reaction rate is pH dependent due to the requirement for a thiol anion. For glutathione, the pKa is approximately 8.5, so at neutral pH the concentration of GS$^-$ will be approximately 3% of the concentration of GSH. The equilibrium between GSH and its associated anion (GS$^-$) is indicated by the symbol "pH=7" next to its associated double-arrowhead line.

Each compound is shown in a box and the transformations (e.g. reactions) between the compounds are shown as lines with arrowheads. If the reaction is catalyzed by an enzyme (e.g. GSH Reductase or GSH Synthase) the name of the enzyme is next to the associated line with arrowhead. The non-catalytic reactions shown are all thiol-disulfide exchange involving a glutathione ion as indicated by the GS$^-$ label next to the associated line with arrowhead.

Note that the total number of thiols is preserved by each exchange reaction (as is the total number of disulfide molecules). Therefore, it is just the mix that is changed. Each SAMC molecule entering the cell would increase the concentration of disulfides relative to thiols. But due to the enzyme glutathione reductase, the concentration of glutathione disulfide (GSSG) inside the cell is kept low (and is normally regulated within cells to approximately 3% of the GSH concentration), which in turn prevents (via exchange reactions) the concentrations of the other disulfides in the cell from increasing. In effect, the eventual formation of GSSG becomes a "sink" for excess disulfides, because the glutathione reductase enzyme will convert the extra GSSG molecule into two thiol molecules. Therefore, the anticipated result is that each new SAMC molecule entering the cell leads to the temporary formation of a GSSG molecule along with the net production of reduced cysteine and allyl mercaptan, through a variety of paths. Also illustrated, some of the cysteine can be used within the cell to produce more glutathione.

Figure 3:
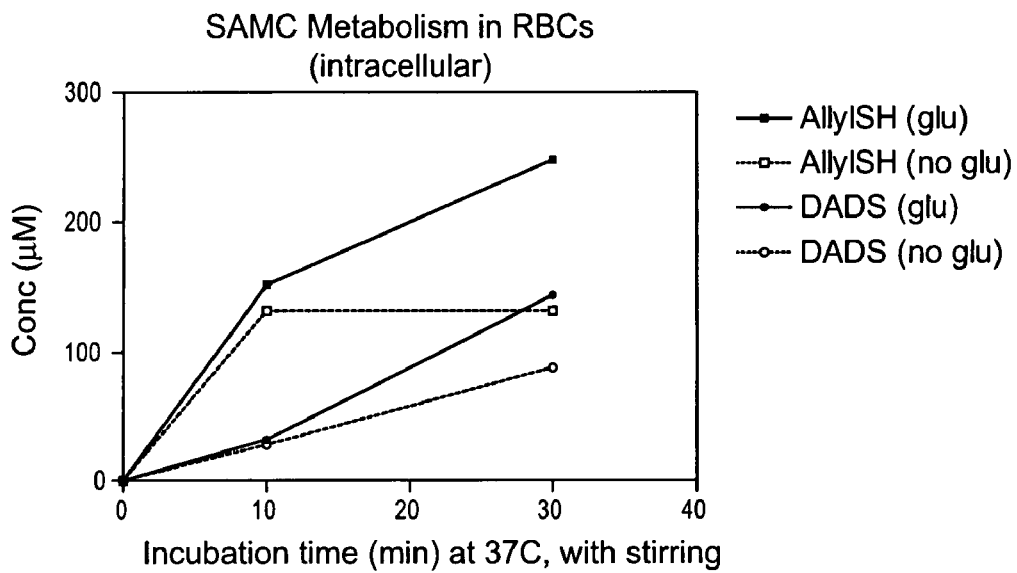
FIG. 3 is a graph showing the significant intracellular formation of AllySH and DADS from SAMC.

The experimental results are graphed in FIG. 3. The formation of AllylSH and DADS was determined at incubation times of 10 and 30 minutes, both with glucose (10 mM) and without glucose in the medium.

The intracellular formation of AllylSH is seen to be significantly higher with glucose added to the medium. The significant effect of glucose is due in part to the energy requirement for the reduction of GSSG to GSH by glutathione reductase, and the need for this "reductive power" to increase the concentration of thiols relative to the concentration of disulfides. As can be seen from the illustration in FIG. 2, in the absence of glutathione reductase activity there will be a buildup of GSSG. Energy is also consumed by any production of additional GSH from the cysteine that has been added to the cell. So, without energy input, the stored energy within the RBCs will decline and the ability to reduce the SAMC to allyl mercaptan and cysteine will also decline. However, the AllylSH will continue to gradually oxidize to DADS (because there is some exposure to oxygen) after the RBCs become metabolically inactive due to energy starvation.

The effect of the depletion of energy in the cells deprived of glucose can be seen in the dramatic lack of increase in AllylSH for these cells after the initial rise. But the cells that were provided with glucose continued to produce AllylSH, with the concentration rising significantly over a 30 minute duration.

The assay of the "intracellular" AllylSH and DADS shown in FIG. 3 also includes the cellular membrane, so some of the AllylSH and probably a large portion of the DADS shown in the figure was actually contained in the membrane, not in the cytosol of the RBCs.

6.1.2.2 Extracellular Antioxidant Production

Figure 4:
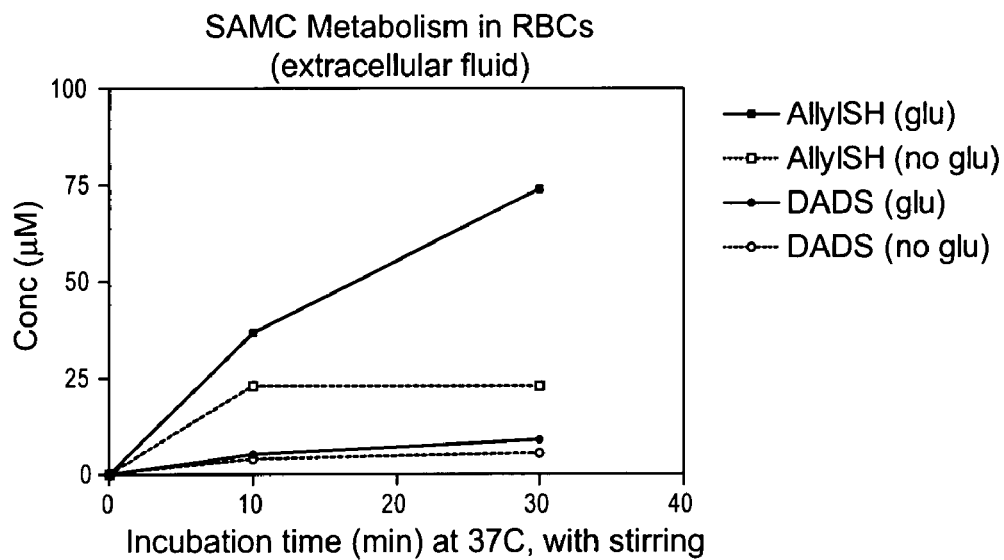
FIG. 4 is a graph showing the significant extracellular presence of AllylSH and DADS as a result of lipid membrane permeability.

Interestingly, AllylSH was also found in the extracellular fluid, as is indicated in FIG. 4 which shows the extracellular concentrations of AllylSH and DADS that was observed during the same experiments that were described in the previous section. For the metabolically active RBCs (those fed glucose) the extracellular AllylSH concentration continued to rise significantly, but for the glucose starved RBCs there was no increase in AllylSH after the initial rise. The gradual rise in DADS is probably due to oxidation of the extracellular AllylSH (due to the presence of oxygen) and is concentration is lower than that indicated by the corresponding intracellular assays of DADS (probably due to the partitioning of the DADS between the aqueous extracellular buffer fluid and the lipid membrane of the RBCs).

These results were not unexpected by the applicant. In fact, one of the primary goals of these experiments was to demonstrate the applicant's theory that the intracellular allyl mercaptan (produced, in effect, by the reductive power provided by glutathione reductase) would diffuse through the membrane to the extracellular fluid, thereby providing an extracellular antioxidant that remains coupled (via the return diffusion of DADS and its subsequent reduction) to the intracellular antioxidant network.

This antioxidant mechanism would be analogous to that observed in macrophages which are able to actively import cystine, reduce it internally to cysteine, and export the cysteine into the cellular environment (see section 3.1.2.3 above).

But the membrane permeability of DADS and AllylSH would be a general property of lipid membranes, and the intracellular antioxidant network is a general property of cells, so this mechanism would be expected to be operative in a broad range of cell types (essentially, every type of metabolically active cell).

The extracellular AllylSH can (and will) participate in thiol-disulfide exchange reactions with the disulfide and mixed disulfide molecules in its environment. In this case, the AllylSH will react with the SAMC to form DADS and cysteine. The DADS can then diffuse into the RBC and eventually become reduced to AllylSH again, which can then recycle to the exterior of the RBC.

The extracellular cysteine that was formed may further react with SAMC to form AllylSH and cystine. This cystine may further react with AllylSH for reform cysteine and SAMC again. The SAMC may further react with AllylSH to form cysteine and DADS. This DADS may enter the RBC and eventually become reduced to AllylSH. It can be seen that these various extracellular thiol-disulfide reactions, while apparently random, tend to include the formation of DADS and a thiol as at least an intermediary, and that this DADS can enter the RBC and eventually become reduced to AllylSH. Therefore, there is a gradual conversion of extracellular disulfides and mixed disulfides to extracellular thiols, with the intracellular reduction of DADS (via the eventual intracellular formation of GSSG and the enzymatic reduction of GSSG by glutathione reductase) as a driving force.

This in vitro experiment has demonstrated the coupling of the intracellular antioxidant network to the extracellular environment by using diffusion and exchange reactions to semi-randomly distribute the oxidized product until it shows up as intracellular GSSG, which is then rapidly removed by the enzyme glutathione reductase (with 2 GSH produced in the process). This results in the creation of a generally reductive environment at the expense of the energy provided to glutathione reductase to drive the system and this reductive environment extends into the extracellular environment.

The ability of DADS to enter the cell through the cell membrane and be metabolized to AllylSH was already well established (PM59:A688). And the mechanism of thiol-disulfide exchange reactions is well known. The theory by the applicant, confirmed by these experimental results showing the efflux of AllylSH through the cell membrane to the extracellular environment, has now completed the loop, demonstrating that a membrane permeable thiol that can reduce an extracellular disulfide and be concurrently oxidized to form a membrane permeable disulfide can further cycle (and recycle) to form a continuously operating extracellular antioxidant system.

6.2 Methods of Administration 6.2.1 Oral Administration

A variety of formulations for the oral administration of bound allyl mercaptan in nutraceutical and dietary supplement form are included in the applicant's co-pending application US2005/0260250A1, which is included here by reference. As described above, allyl mercaptan is a good choice for use as a model compound because of its availability as an FDA approved food additive, its history of use as a food additive, and its history of use as a metabolite of dietary alliums. The initial experiments were with protein containing beverages (e.g. apple juice), then a dietary supplement capsule was developed.

The binding of allyl mercaptan to a larger molecule (as taught in US2005/0260250A1) is important because of the strong mercaptan odor and taste of this molecule in unbound form. Even a small concentration of unbound mercaptan can be objectionable, as was recently evidenced by the appearance of a mysterious strong odor in Manhattan on Jan. 8, 2007 that nauseated many people. Even a few well dispersed ounces of (for example) ethyl mercaptan could be enough to stink up all of Manhattan (NYTIMES2001:0121A). Although the source of the odor was not was not found, it was described as having a mercaptan-like smell and may have been a natural product produced by micro-organisms in the coastal marshes (NYTIMES2001:0121 B).

Because the present invention involves the presence of free thiols (at least within the organism), the issue of the odor of mercaptans must be addressed, regardless of the specific type of thiol that is being utilized. However, the applicant has discovered that when bound to larger molecules (e.g. by disulfide bonding the allyl mercaptan to the cysteine of proteins to form a prodrug) significant amounts of bioavailable thiol can be administered without any objectionable odor or taste. This technique is likely to be effective with whatever type of thiol that is being utilized in any specific implementation of this invention.

When binding AllylSH to protein, it can be preferable to use DADS as a starting ingredient because it is less odorous than AllylSH and is also FDA approved for use as a flavoring agent in food. The disulfide (DADS) will readily form mixed disulfides with the protein cysteine, just as AllylSH does with cystine. Because the molecular weight of the DADS molecule (which provides two allyl mercapto groups) is nearly equal to twice that of AllylSH (146.26 vs. 74.14), an equal weight of DADS or AllylSH can be used to provide a nearly equivalent result.

When used as a flavoring agent in condiments or meats (TX589.F46131:17), the amount of DADS used is reported to be 7 parts per million (e.g. 2.8 milligrams for a 400 gram serving of meat). When used according to the present invention as a nutraceutical or for other medicinal purposes, a higher dosage than this is required.

Daily consumption of a crushed clove of raw garlic has been associated with health maintenance and is recommended for successful aging (E185.96.D368:107). While this can be expected to metabolize to approximately 10 mg of AllylSH in the body (PM59:A688), the consumption of garlic in this form is somewhat distasteful, burns the mouth, and is not recommended by the applicant because the alternative consumption of the equivalent dosage of protein bound allyl mercaptan can be pleasantly tasteful (depending on the taste of the protein) and nontoxic.

An equivalent dosage in dietary supplement form could be provided by, for example, two capsules containing 5 mg of AllylSH each (e.g. in the form of protein bound allyl mercaptan). The applicant has found that up to 10 mg of allyl mercaptan (or DADS) can be combined with whey protein to produce a reasonably sized capsule (size "0") for dietary supplement use, although it is anticipated that further improvements could increase this amount.

However, this usage example provides what the applicant regards as the target minimum daily dosage for the purpose of health maintenance. As will be seen in further examples below, a daily dosage in the range of 30 to 60 mg has been shown to be safe and effective. On an experimental basis, the applicant has consumed up to 240 mg per day for weeks at a time.

Administration in the form of nutraceutical foods is a very convenient way to achieve a dosage within this range. Even a beverage such as apple juice can contain as much as 10 mg per 8 ounce glass without any objectionable flavor or odor. At a dosage of 5 to 20 mg per serving, multiple servings of a variety of nutraceutical foods could be consumed per day to achieve a target cumulative dosage in the 30 to 60 mg range.

Even at 240 mg per day, the dosage is much lower than the dosage that has been used successfully in some experiments involving animals, so even higher dosages are anticipated to be beneficial for specific treatments, especially for the treatment of acute conditions. For example, in a study of the prevention of acetaminophen poisoning in mice (PHYRES3: 50), the dosage of SAMC used was up to 200 mg/kg, which would correspond to a dosage of 5,000 mg of AllylSH for a 70 kg adult human. The low toxicity of protein bound allyl mercaptan and of related compounds such as SAMC can be expected to allow dosages up to this to be utilized, when necessary.

6.2.2 Other Methods of Administration

The methods of administration are not limited to oral administration. For example, the applicant has produced products such as skin lotions and toothpaste containing bound DADS or bound allyl mercaptan. In general, the term administration as used herein is intended to cover any method that causes a compound to enter into the body of an animal, either orally, by injection, or by any other means.

6.2.3 Use of Other Organosulfur Compounds.

The present invention has been illustrated according to the use of the model compound allyl mercaptan and prodrugs for allyl mercaptan to produce a membrane permeable thiol that can be oxidized to form a membrane permeable disulfide. But other thiols or prodrugs for thiols can also be shown to have similar properties.

For example, the organosulfur compounds from onion tend to contain propyls instead of allyls (AM17:903). Just as the compound diallyl disulfide can be reduced to allyl mercaptan, the onion derived compounds n-propyl disulfide and n-propyl allyl disulfide can be reduced to the thiols propyl mercaptan and allyl mercaptan. Each of these disulfides and thiols is likely to be membrane permeable, and both propyl mercaptan and allyl mercaptan are FDA approved food additives, so these thiols and the disulfides that can form from their oxidation are likely to be non toxic.

Similarly, the organosulfur compounds derived from cabbage tend to contain methyl groups (JFP60:67), with dimethyl disulfide being reducible to methyl mercaptan. Both the disulfide and the thiol are likely to be membrane permeable, and methyl mercaptan is an FDA approved food additive, so this thiol and the disulfides that can form from it are likely to be nontoxic.

Studies of radioprotective substances have shown that thiol compounds with more than 5 carbon atoms are ineffective in protecting animals from radiation exposure. My interpretation of this is that when thiols that are larger than this are consumed, they eventually form mixed disulfides with glutathione which are excreted by the GS-X pump from cells (and ultimately from the host). Therefore, thiols that are larger than this are likely to be ineffective.

In general, it is expected that mercapto radicals containing up to 5 carbon atoms, will share many of the properties that are attributed to allyl mercaptan (and its disulfide) in this description. Therefore, these constitute alternative substances that may be utilized, provided that they are nontoxic. The present invention is intended to apply to the general class of compounds that have been presented in this section.

6.3 In Vivo Demonstrations of Efficacy

Initial tests to confirm the bioavailability of AllylSH following the consumption of protein bound allyl mercaptan were performed utilizing a breath allyl methyl sulfide (AMS) assay that is offered commercially by Plant Bioactives Research Institute, Orem Utah (JAFC53:1974). Various garlic related compounds contain allyl mercapto groups and share the property of producing a known quantity of breath AMS after consumption. The test successfully showed significant AMS production with a good release profile, being well spread out over time (presumably due to the time required for protein digestion) which is beneficial because it minimizes potential "garlic breath". However, the total AMS production, as indicated by the area under the curve, was less than expected. (The reason for this is still unknown, but it is probably due either to some difference in the metabolism of the compound (e.g. incomplete digestion) or a non-linearity in their assay procedure relative to the products that they normally test.)

Subsequent to this initial test, the applicant and several friends and relatives have used the capsules as a dietary supplement on a regular basis. Each person who has evaluated the capsules has done so based on informed consent, having read and signed a "Nondisclosure and Product Evaluation Agreement". The capsules have been provided free of charge (not for sale).

After the applicant had consumed these capsules for two years, a medical check-up and laboratory report showed these changes from a similar checkup two years previous:

| Weight | 155 lbs | (was 175) |
| Blood Pressure | 140/80 | (was 150/80) |
| Pulse rate | 60 | (was 70) |
| Temperature | 97.6 | (was 98.6) |
| HDL Cholesterol | 60 mg/dL | (was 45) |

-continued

| LDL Cholesterol | 128 mg/dL | (was 152) |
| Triglycerides | 128 mg/dL | (was 290) |

These figures show various improvements.

A plasma amino acid analysis was also performed, which showed a cyst(e)ine level of 4.4 umol/dL, which was well within the "reference interval" of 0.3 to 5.6. However, beyond that it was not very useful because the assay did not distinguish between cysteine and cystine, and therefore provided no information about the plasma thiol/disulfide ratio.

Subsequently, an alternative, simpler assay procedure for the thiol/disulfide ratio was found in the literature. Other researchers had determined that the level of plasma albumin correlates linearly with the thiol/disulfide redox (BLOOD92:59, in which paper this redox relationship is expressed by the cystine/thiol ratio).

Protein thiol concentrations, principally the albumin (which has an exposed thiol residue at Cys34) are 25- to 50-fold higher than the free cysteine concentration in human plasma (FRBM33:1290). Therefore albumin is an antioxidant in the plasma, just as the free cysteine is. The percentage of reduced albumin tends to be lower in patients with various conditions or diseases such as hepatic disease, diabetes, renal disease, temporomandibular joint disorders, aging, and tiredness or fatigue (FEBSJ273:3346).

The oxidation of albumin is a similar process to the oxidation of cysteine, because it is actually due to the formation of a mixed disulfide with cysteine (FEBSJ273:3346). The oxidized albumin is cleared from the plasma 3 times more quickly than unoxidized albumin and therefore the concentration of albumin in circulation is a direct function of the plasma thiol/disulfide ratio (COCNMC2:227).

A detailed study of the relationship between the albumin concentration and age was performed using 86 randomly selected healthy human subjects aged primarily from 20 to 80 (BLOOD92:59). Both the albumin concentration and the cystine/thiol ratio were measured, and were found to be correlated with each other. Analysis confirmed the negative correlation between plasma albumin concentration and age ($r=-0.57$, $P<10^{-5}$), if tested by Pearson's test (BLOOD92:59). As the cystine/thiol ratio increased from 2 up to 12 (indicating increased oxidation), the albumin concentration declined linearly from 800 uM to 600 uM (FIG. 2 of BLOOD92:59).

The relationship between the albumin concentration and the cystine/thiol ratio was then confirmed by a longitudinal study on a single healthy individual in the sixth decade of life to determine whether the correlation between longitudinal changes in plasma albumin level and plasma cystine/thiol ratio could be confirmed in a single person over time (in contrast to showing this relationship across a population). Plasma cystine/thiol ratios and albumin levels were determined at 39 randomly chosen time points during a 2-year observation period (BLOOD92:59). The results confirmed that there is a significant correlation between them ($r=-0.61$; $P<10^{-5}$).

This method of determination of the plasma redox is of great interest to the applicant because the albumin concentration is one of the standard measurements performed in medical lab reports. This meant that historical data was available that could show the age-related decline in albumin level and confirm its reversal with the administration of dietary supplement capsules containing protein bound allyl mercaptan. It could also be used to confirm that the effect was reversible (by discontinuing the administration of the capsules) and repeatable (by the resumption of the administration of the capsules).

The historical albumin levels for the applicant are as follows:

| Age 37, | 4.9 g/dL | Prior to any AllylSH consumption (medical records start) |
| Age 46, | 4.5 g/dL | (next comprehensive medical examination) |
| Age 50, | 4.6 g/dL | ~5 mg AllylSH/day (Experiments with beverages started) |
| Age 52, | 5.0 g/dL | Consuming ~20 mg AllylSH each day |
| Age 53, | 5.0 g/dL | Consuming ~20 mg AllylSH each day |
| Age 55, | 5.1 g/dL | Consuming 180 mg AllylSH each day |

This historical data can be seen to confirm that the age related decline in the albumin level (4.9 g/dL down to 4.5 g/dL) was reversed when the experiments with AllylSH started (occasional AllylSH consumption) and was fully reversed once the amount of AllylSH consumption reached ~20 mg/day. Increasing the level of AllylSH consumption to 180 mg/day had little additional effect.

Over the next 3 months, an experiment was performed to determine whether this effect was reversible, and then to see if the effect was repeatable:

| +1 mo., | 4.9 g/dL | Discontinued AllylSH consumption |
| +1 mo., | 4.5 g/dL | " |
| +1 mo., | 4.7 g/dL | Consuming 180 mg AllylSH/day |

These results can be seen to show that the reversal was slower than expected (it took two months for the decline to occur), the decline was less than expected, and the recovery was slower and to lesser extent than expected. Based on the previous decline from age 37 to age 46, the extrapolation of this decline calculates to an expected albumin level at age 55 of approximately 4.1.

Figure 6:
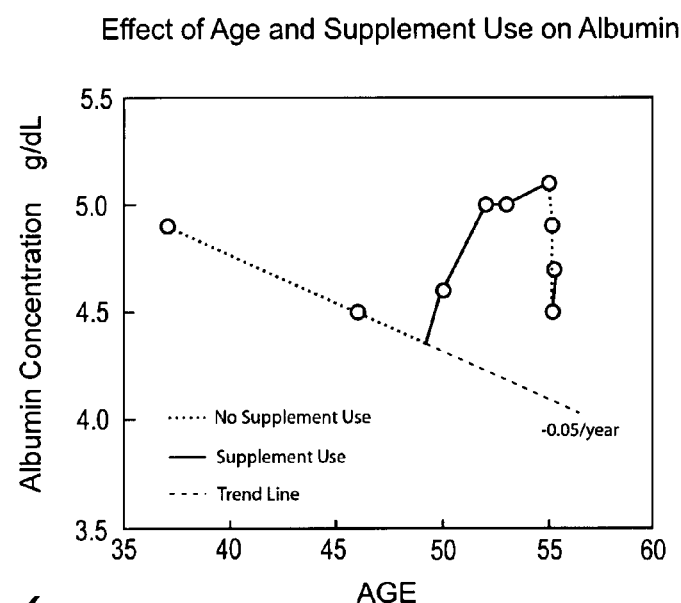
FIG. 6 is a graph showing the response of the plasma albumin level to the administration of antioxidant dietary supplement capsules.

A graph of this experimental data is shown in FIG. 6, with the periods of AllylSH consumption (dietary supplement use) indicated by solid lines. The age related initial decline of approximately −0.05 per year is also shown extended by a dotted trend line. The presumed departure from the trend that occurred when the supplement use was started is indicated by the first solid line segment.

This experimental data indicates the expected trend but both the response to discontinuation and the response to resumption were much slower than the expected rate. This may indicate the presence of a pool (of DADS in cellular membranes?) that takes a long time to build up and then a long time to decline.

The turnover rate for albumin is reported to be very rapid (AJRCCM162:1539), therefore the delayed response is unlikely to be caused by a slow "albumin response time". In hindsight, if instead of doing the experiment over a 3 month period, a 6 months period had been used, because this would have shown a more complete response (on the reasonable assumption that the incomplete response seen in the experimental data is due to a slow response time).

Without wanting to be bound to a particular theory, the applicant notes that the amount of AMS produced after the consumption of protein bound allyl mercaptan was lower than expected. As noted above, the digestion of this compound is also different from that of other AMS producing compounds in that it involves the digestion of protein. With the other products, AllylSH is likely to be produced in the gut, but with protein bound allyl mercaptan, normal protein hydrolysis (breaking the peptide bonds between the amino acids) will produce the disulfide SAMC, which is actually an amino acid. The SAMC amino acid molecule may be transported out of the digestive system without releasing the AllylSH in the digestive tract.

Because AMS (Allyl Methyl Sulfide) is S-methylated allyl mercaptan, the "thiol S-methyltransferase" enzymes are likely to be involved (QP601.E515:131, BBA46:217) in its formation. These enzymes are distributed in a variety of tissues, but the concentrations are highest in the digestive and excretory tract (stomach mucosa, cecal mucosa, colonic mucosa, liver, and kidney) and lung, indicating that their primary purpose is probably the detoxification of ingested or inhaled substances (QP601:E515:131). If the digestion of protein bound allyl mercaptan bypasses these enzymes, the later production of AllylSH and DADS would not produce as much AMS. And if the DADS forms a pool in cellular membranes (due to its high partition coefficient), it may persist in the body for a long time without ever encountering a thiol S-methyltransferase enzyme.

It is also of note that when a DADS molecule leaves a cell it is likely to soon encounter the membrane of a nearby cell. Given its high partition coefficient, it is also likely to remain in the second cell for a length of time that is significantly longer then its transit time between cells. Therefore, DADS is very unlikely to travel very far in the body very fast.

This theory would explain both the low rate of AMS production after administration and the existence of a DADS pool with a long time constant.

6.4 The Mitigation of Disease

Various diseases and conditions are known to be associated with cysteine depletion. Cysteine depletion is considered to be any condition in which the cysteine concentration is sufficiently below the optimum level that it adversely affects the animal, and therefore need not be complete depletion.

Some diseases may be caused as a direct result of the cysteine depletion itself while other diseases or conditions may merely cause cysteine depletion. In this case, a different cysteine depletion related disease may be caused or exacerbated by the aforementioned disease or condition that causes cysteine depletion.

One disease that the applicant has determined to be cysteine depletion related is arsenicosis. Because cysteine depletion is not commonly recognized by other researchers as being related to this disease, for this example the relationship between cysteine depletion and the disease will be presented in detail. Other diseases for a relationship with cysteine depletion has been generally accepted by other researchers will be presented afterwards as further examples, and in less detail.

6.4.1 The Mitigation of Arsenicosis

Arsenicosis is the disease that is caused by arsenic poisoning and is currently a major health problem in West Bengal, India and in Bangladesh due to the consumption of arsenic contaminated well water. The problem will get much worse with time, because many of the symptoms are slow to appear, and there is no easy solution to the underlying environmental problem that has been created. The book "Venomous Earth—How arsenic caused the world's worst mass poisoning" (RA1231.A7M44) does a good job of presenting the scope of the disaster.

An estimated 35 million or more people in Bangladesh have been drinking arsenic contaminated water from "tube-wells" (BWHO78:1093) that were drilled mostly in the 1970s, before it was realized that there were underground natural geographic formations in the area containing inorganic arsenic. Because of the delay in the development of symptoms, many thousands of wells were drilled before (and after) the problem was discovered, and these wells remain a primary source of "clean" drinking water for many villages. Shallow tube wells are the main source of drinking water for 97 percent of the rural people in Bangladesh (APJCP4:7).

Drilling deeper wells would avoid the layer of underground arsenic, but drilling a deep well can cost up to 45 times as much to drill as the shallower tube wells (RA1231.A7M44: 170). By now, the water has been used extensively for the irrigation of rice, which has permanently contaminated the soil and is producing arsenic contaminated rice (RA1231.A7M44), so even new wells would not completely solve the problem. The scale of this environmental disaster is greater than any seen before, even exceeding that of the nuclear accident in Chernobyl (RA1195.E48:118).

The scope of the problem (and the expense of the proposed solutions) has led to inactivity. The developing medical problems will potentially overwhelm the health care system, making a "personal care" alternative for those who are suffering a potentially important short-term component of any long-term solution to the problem.

6.4.2 Arsenic Toxicity and the Symptoms of Arsenicosis

Clinical features of arsenicosis include hyperpigmentation, hyperkeratosis, nodular keratoses (usually on the palms and soles), skin lesions, weakness, anemia, burning sensations, solid swelling of legs, chronic lung disease, liver fibrosis, gangrene of the toes, neuropathy, skin cancer, and various internal cancers (especially of the lung, bladder, liver, or kidney) (JESH38A:141, EHP108:671). The nodular keratoses can develop into skin cancer.

Hyperpigmentation has been described as raindrop shaped discoloration spots, diffuse dark brown spots, or diffuse darkening of the skin on the limbs and trunk (EHP108:617). It is typically the first symptom of arsenicosis to appear, and is also the most prevalent symptom. There is commonly a progression from hyperpigmentation to nodular keratoses and/or hyperkeratosis, to skin cancer (typically appearing first at the location of a nodule (HTOX8:99)), and then the development of cancer at other locations in the body. This progression takes years to decades to occur and explains the relative occurrence of symptoms typically observed (hyperpigmentation>nodular keratosis>skin cancer>systemic cancer).

In general, inorganic arsenic consumption is much more toxic than the consumption of organic forms of arsenic (e.g. from seafood such as shrimp) (QH545.A77:117). The inorganic arsenicals from groundwater are typically either based on arsenite ($AsO_3^{2-}$), with the arsenic in oxidation state As(III) or on arsenate ($AsO_4^3$), with the arsenic in oxidation state As(V). The detoxification process that occurs in the body converts the inorganic arsenic compounds to the organic arsenic compounds MonoMethyl Arsenic acid (MMA) and DiMethyl Arsenic acid (DMA), which are then excreted in feces and urine.

A relationship between glutathione and arsenic toxicity is indicated by a study of genetic factors in patients with arsenic-induced skin cancer. This study found that the glutathione S-transferase enzymes were more frequently mutated in these patients (relative to a control group) and that those who had at least one null or variant of GST M1, T1, or P1 had a 5-fold greater risk of developing skin cancer (TAP206:198).

As will be seen from the discussion below, much of the toxicity of arsenic is due to its interactions with biothiols, especially the SH groups of proteins. Because As(III) reacts more readily with thiols than AS(V) does, it is more toxic (QH545:A77:4). Additional toxicity can result from thiol depletion. To a lesser extent, arsenic can also damage molecules that do not contain SH groups (such as DNA). Although these other reactions are fewer in number, they can have serious long term consequences (such as the development of cancer).

Arsenic compounds (arsenicals) are also beneficially used as chemotherapeutic drugs, although some types of cancer cells can acquire resistance to these drugs. Typically, the acquisition of resistance to one of these drugs will also result in these cancer cells being resistant to other, seemingly unrelated, chemotherapeutic drugs. This phenomenon of "Multi-drug Resistance" has been extensively researched.

Because thiols (especially glutathione) are important in the detoxification of arsenicals in the body, and also because the applicant has observed that many of the reported symptoms of arsenicosis are similar to the reported symptoms of glutathione depletion, and also because the metabolism of arsenicals is known to deplete glutathione, the applicant has investigated the possibility that the observed increase in arsenic toxicity among some populations is due to glutathione deficiency.

Although the applicant believes that that the toxicity of arsenic exposure is related to the thiol (e.g. glutathione) content of the host, this is not a widely known (or accepted) position among the arsenicosis research community. For example, although the dietary protein of affected groups has been surveyed, the SAA content of the protein has been ignored (e.g. all proteins have been considered equal). Similarly, although the dietary content of some types of vitamins and antioxidants have been surveyed, the thiol based vitamins (e.g. thiamin) and antioxidants (e.g. the SAA content of protein) have been ignored.

As another example, the most authoritative book on arsenicosis from drinking water ("Arsenic In Drinking Water" (RA1231.A7N38)) makes little mention of glutathione's role in the detoxification of arsenic. Although it does describe several times the toxic reactions of arsenicals with the SH groups of proteins, it does not consider the detoxification properties of simple, non-protein thiols such as glutathione. The most prominent mention of glutathione in the book is its role in the conversion of As(V) to As(III) (RA1231.A7N38: 150), which to the reader would imply an increase in toxicity.

Although the following description relies heavily on the published research results of others, it is largely the extensive research on the use of arsenicals for cancer chemotherapy (where the protective effect of glutathione and other thiols is well known) that provides relevant results for the issue at hand. Although the chemotherapeutic use of arsenicals intentionally induces toxicity, the things that can interfere with this are of great interest to the applicant in devising ways to reduce the toxicity of environmental arsenic exposure. Therefore, because the applicant is applying an alternative perspective to much of this research, it is being presented here rather than in the "published art" section of this patent application.

6.4.3 Roles of Thiols in Arsenic Detoxification

Thiols (especially glutathione) play many roles in the detoxification of arsenicals. These can be divided into interactions with inorganic arsenic, the formation of glutathione conjugates for the excretion of arsenicals from cells, and the methylation of arsenicals to monomethylarsonic acid (MMA) and dimethylarsonic acid (DMA), the major arsenic products that are excreted from the body.

6.4.3.1 Inorganic Arsenic Forms Complexes with Thiols

The ability of arsenicals to inhibit (or occasionally stimulate) various enzymes is well known to biochemists. For example, the classic, 3-volume text "Enzyme and Metabolic Inhibitors" devotes 195 pages to various arsenicals, including detailed descriptions of many of their effects on animals, but also includes recommendations against their general use in experiments due to their non-specificity (QF601.W38V3: 595). Because perhaps 50% of enzymes contain thiols (or disulfides) that are sensitive to "SH reagents", the arsenicals can affect such a large number of types of enzymes (and other proteins) that it can be hard to attribute any observed results to any specific effect. Modern biochemists have a wide variety of other, more specific, enzyme inhibitors available, so they rarely choose to use arsenicals in experiments.

Arsenic is well known to accumulate in hair and nails. This accumulation is due to their high concentration of "SH" groups and disulfides (RA1231.A7N38:177). This could be viewed as an example of the detoxification of arsenicals by thiols, in this case by the non-essential "SH" groups in these proteins.

Perhaps more relevant to the subject at hand is the protection that non-protein thiols can provide. To the extent that these other thiols successfully "compete" with the enzymes (and proteins), the formation of complexes between the arsenicals and these thiols will "protect" the enzymes. These thiols are normally derived from dietary cyst(e)ine (and dietary alliums), which naturally provide a level of protection (conversely, their deficiency would lead to unnecessary toxicity from the arsenicals that would otherwise be detoxified).

In some circumstances, the application of a more powerful chelating agent has been shown to be beneficial. The invention of arsenical war gases in World War I (e.g. Lewisite) led to the development of "British Anti-Lewisite", a dithiol compound that has two "SH" groups in close proximity, which results in preferential chelation of arsenicals relative to isolated thiols (US002432797), thereby providing protection via competition.

Even when an enzyme becomes inactivated by an arsenical, in many cases it can be fully reactivated by glutathione (S97:356). For example, if an SH group on a protein (e.g. PSH) becomes "blocked" by the arsenical (e.g. becomes PSAsR, where R is the remainder of the arsenical), a glutathione molecule (GSH) floating by can participate in an exchange reaction, restoring the activity of the enzyme (PSH) and producing a less toxic conjugate (GSAsR). (These reactions probably actually involve thiolate ions (e.g. PS$^-$ and GS$^-$), as all thiol-disulfide exchange reactions do.)

The applicant notes that the formation of a complex between a thiol and an arsenical results in the depletion of a thiol that would otherwise be biologically active. If thiols are plentiful, this is clearly beneficial, but if thiols are deficient, this becomes a secondary source of toxicity. People exposed to arsenic therefore have a higher dietary requirement for thiols (and thiol precursors) than the general population does.

Arsenic increases the formation of oxygen radicals, which is the mechanism by which it induces the apoptotic killing of cells. The production of these radicals has been implicated as arsenic's mechanism of producing genetic damage (PNAS98:1643, TOXICOL79:195). These oxygen radicals can be quenched by glutathione, which in turn produces an increase in oxidized glutathione (GSSG) as it protects the cell. Consumption of garlic has also been shown to reduce arsenic toxicity and chromosomal damage, presumably due to its antioxidant activity (EMM21:383).

Although glutathione (and other thiols) rapidly reduce As(V) to As(III), the As(III) can then form a less toxic conjugate with glutathione (RA1231.A7N38:150). A major conjugate that is formed has been shown to be Arsenic TriGlutathione (ATG), which consists of three glutathione molecules conjugated to a single arsenic atom, and forms spontaneously in solution (CRT6:102). The rate of ATG formation is proportional to the cube of the GSH concentration, and therefore declines precipitously during GSH depletion (JBC275:33404).

Arsenicals (especially ATG (CRT10:27)) inhibit the activity of glutathione reductase, which exaggerates the increase in GSSG (and loss of GSH) during initial exposure, but after chronic exposure this is compensated for by a dramatic up-regulation of the mRNA for glutathione reductase enzyme synthesis, resulting in a net increase in glutathione reductase enzyme activity (TOXSCI70:183) and producing an acquired tolerance to future arsenic exposure.

The applicant notes that for this naturally induced tolerance to be effective, there must be enough cysteine available for the cell to synthesize the requisite glutathione.

It has been determined that cells that are resistant to arsenic toxicity typically have an up-regulation of the genes involved in the production of the glutathione detoxification proteins (glutathione synthesis (TOXSCI70:183), glutathione reductase (TOXSCI70:183), glutathione transferases (TAP183:99, MOPM60:302), and the multidrug resistance transport proteins (MOPM60:302)).

Conversely, reducing the level of glutathione (e.g. via the administration of buthionine sulfoximine (BSO) or ascorbic acid) has been shown to increase the cytotoxicity of chemotherapeutic arsenicals (BLOOD93:268, BLOOD98:805, CCP52:47). FIG. 10 of CCP52:47 shows photographs of leukemia cell cultures that have received these treatments, dramatically showing the increase in the "kill rate" of arsenic trioxide when either BSO or ascorbic acid is co-administered.

Interestingly, it has been shown that when leukemic cells evolve to become resistant to the chemotherapeutic drug "TPA", their natural glutathione level decreases, making these cells especially sensitive to the arsenic trioxide. Thus, it can be beneficial to initially administer TPA to leukemia patients, with the plan of later administering arsenic trioxide to those patients whose leukemia becomes resistant to TPA (BLOOD97:3931).

6.4.3.2 Only Glutathione Conjugates of Arsenic are Excreted from Cells

The mechanisms involved in the excretion of the glutathione-arsenical conjugates from the cell has also been extensively studied within the context of multidrug resistant cancer cells. Regardless of whether the conjugate is formed non-enzymatically or it is formed by an enzyme (e.g. a glutathione transferase), the actual transport of the conjugate through the cellular membrane is performed by a trans-membrane multidrug-resistance protein (MRP) such as the MRP-1 or MRP2 pump (MOPM60:302, JBC275:33404). Chronic arsenic exposure up-regulates the expression of the genes for these proteins (MOPM60:302).

This excretion of arsenic from cells by an MRP been shown to require the arsenic to be complexed to glutathione, either in the form of ATG, or as MethylArsenic DiGlutathione (MADG), or as DiMethylArsenic Glutathione (DMAG) (JBC275:33404), because the depletion of glutathione in the cells reduces the excretion to less than 2% of the control rate (JBC275:33404). The MADG and DMAG excreted from liver cells into the bile has also been shown to rapidly break down to the MMA and DMA that are excreted from the body.

Therefore, the formation of MADG inside the cell is critical for the excretion of arsenicals both from the cell and from the body. Because the rate for this depends on the 4th power of the GSH concentration (JBC275:33404), it can again be seen that glutathione depletion in cells drastically restricts their ability to excrete arsenic.

6.4.3.3 Detoxification of Arsenicals via Methylation Requires Glutathione

The methylation of arsenic to either MMA or DMA is the only significant path for the excretion of arsenic from the body. Newly ingested arsenic can be methylated and excreted very quickly, with typically 40% of it excreted directly from the liver to the bile during the first hour after consumption (JBC275:33404). But the remaining 60% enters the rest of the body and will take a significantly longer time to return to the liver (which is the only path to excretion).

The only significant dietary source for the methyl groups that are used for methylation reactions in humans is the amino acid methionine (Met). Typically, the methyl group from Met is first used to form SAM-e (S-adenosyl methionine), and then the methyl group is transferred by an appropriate enzyme from the SAM-e molecule to the methyl group recipient.

Methionine is a essential sulfur amino acid (SAA) and can be used to form cysteine if dietary cysteine is inadequate. Another way to look at this is that if Met is consumed by some metabolic process, less cysteine can be formed, thereby contributing to the development of cysteine (and glutathione) deficiency.

Two metabolic pathways have been found for the methylation of arsenic, and they both require glutathione. For cells that express the enzyme "arsenic methyltransferase Cyt19" the methylation step requires glutathione as a cofactor (ATOX79:183). There is also a non-enzymatic reaction that transfers a methyl group from methylated vitamin B12 (methylcobalamin) to arsenite, with glutathione as a cofactor (possibly via the intermediate formation of glutathionylcobalamin) (TAP154:287).

Methylated arsenic (e.g. MMA, DMA) is ~1000× less mutagenic than some inorganic arsenic compounds RA1231.A7N38:150). Therefore methylation is important not only for the excretion of arsenic from the body, but also to decrease the toxicity of the arsenic while it is within the body.

6.4.3.4 Correlation of Arsenicosis Symptoms with Glutathione Depletion

The applicant has observed that the other reported symptoms of chronic arsenic toxicity are similar to those that can result from biothiol deficiency.

Typically, the first visible symptom of arsenicosis is the darkening of the skin (hyperpigmentation)(JESH38A:141). Glutathione deficiency due to poor nutrition is a known cause of hyperpigmentation (ARCHIM138:356). Normal levels of glutathione in skin cells are needed for the feedback inhibition of melanin production. Without the feedback inhibition, the excess production of melanin produces skin darkening, including the formation of brown patches and black spots.

Hyperkeratosis (the thickening, hardening, and cracking of the skin) can be caused by the lack of normal skin loss. The dead stratum corneum cells that form the tough outer surface of the skin are supposed to be continuously shed and replaced with newly cornified cells. The extreme insolubility of the outer surface in vivo is a result of the macromolecular polymerization of various keratinocyte proteins involved in both disulfide and isopeptide bonds (EMM31:5). The cleavage of both types of these bonds is necessary for normal skin loss. This can be shown in vitro, where the combined use of a detergent, a reducing agent (to separate the disulfide bonds via thiol-disulfide exchange reactions), and concentrated chaotropic agents (urea, guanidine-HCl) is necessary to solubilize the skin (EMM31:5).

The applicant notes that a deficiency (or the excess oxidation) of the biothiols that are normally utilized in vivo for breaking these disulfide bonds would cause the thickening and the hardening of the skin, which could also lead to the cracking of the thickened, hardened skin.

Biothiols also inhibit the formation of advanced glycation end-products, another form of undesirable cross-links.

Blackfoot disease is related to poor peripheral circulation, as is the eventual development of gangrene. Endogenous nitric oxide (produced in vivo by the eNOS enzyme) is necessary for good blood flow. The feedback regulation of eNOS involves the nitrosylation (by nitric oxide) of a cysteine residue (in other words, this is an "SH" sensitive enzyme). The applicant notes that this can be reversed by an exchange reaction with a thiol, returning the cysteine residue to its active state. Therefore, the activity of eNOS is determined by the balance between the NO concentration and the concentration of thiols in solution.

Garlic supplement consumption has been shown to increase the fluidity of blood, increasing the red blood cell velocity in the cutaneous capillaries by about 27% (PM56: 668). Dietary alliums increase the activity of eNOS (nitric oxide synthase), increasing the nitric oxide (NO) concentration and improving blood flow (BST23:S136). These effects are probably due to thiol supplementation.

6.4.4 Correlation of Arsenicosis with the Dietary Factors of Populations

There are also well-fed populations drinking arsenic contaminated water that do not develop arsenicosis (e.g. in many parts of the USA). The development of arsenicosis in arsenic exposed populations has been shown to correlate with poor nutrition (i.e. low body weight) (JESH38A:141, IJEP27:871) and the symptoms were shown to significantly improve after 7 weeks of treatment with a high protein diet and arsenic-free water (JESH38A:141).

Experiments with animal models confirmed the lower weight gain and increase in toxicity of arsenic when fed a low protein diet. Rabbits fed a low protein diet have decreased excretion (80%) and higher retention of arsenic (220% greater, in the liver) than arsenic fed controls (TL37:41). In another set of experiments (BDR71:124), arsenic exposed pregnant mice fed a low protein diet (5%) had significantly lower weight gain than controls fed a 20% protein diet (2.73 vs. 6.01), and had a significantly higher prenatal mortality (14% vs. 2.35%). Their offspring also had lower weight (0.72 vs. 0.93) and a much higher percentage of grossly malformed fetuses per liter (24.65% vs. 0.81%).

6.4.4.1 Correlation with Poor Nutrition in India

A detailed study of the relationship between nutritional factors and susceptibility to arsenic caused skin lesions in West Bengal, India (EHP112:1104) presents survey results that support the observation of the applicant that there is a correlation between low dietary sulfur amino acid (SAA) intake (presumably resulting in glutathione deficiency) and toxicity of arsenic exposure.

Table 3 in the article compares the nutrient intake between the cases and the controls, which is used by the authors to identify the nutritional risk factors. Four of these were highlighted in the description of the results. The strongest factor that increased risk was found to be low animal protein intake (animal protein is the best source of SAA content). The applicant notes that almost all Indian Foods that include meat also include garlic or onions (another good source of SAA and thiols).

The next strongest factor was low fiber intake. The authors note that a large fraction of the fiber intake in this population comes from rice intake. Rice has relatively high SAA content compared to other non-animal foods.

The risk from low calcium intake was comparable to that of low fiber intake. If a primary dietary source of calcium is from milk products, then low calcium intake implies low milk intake. In the average US diet, approximately ¾ of the calcium comes from milk products. Because whole milk is a good dietary source for cyst(e)ine, high milk intake correlates with high dietary cyst(e)ine. However, if the reported calcium is from cabbage or broccoli, these are also good sources of SAA and thiols.

The fourth major risk factor was low vitamin C intake. Because vitamin C can partially substitute for glutathione and can protect animals from otherwise fatal glutathione loss (RB170.O96:101), this also indicates the possibility of the arsenicosis symptoms being due to glutathione deficiency. Although high dosages of vitamin C can be used to increase the toxicity of arsenic, the amount of dietary vitamin C (especially for poorly nourished people) is nowhere near the level that is used clinically to cause a decrease in glutathione (e.g. 1000 mg/day).

After adjustment for socioeconomic variables, low folate consumption emerged as a significant risk factor (EHP112: 1104, Table 5). The applicant notes that a major biological function of folate is as a cofactor in the conversion of homocysteine back to cysteine (in effect, enabling the cysteine that metabolizes to homocysteine to complete the cycle) and the most prevalent toxicity from folate deficiency is the accumulation of homocysteine (and consequent depletion of cysteine) (CCHEM51:5).

6.4.4.2 Correlation with Poor Nutrition in Taiwan

A study of the risk factors associated with the development of arsenicosis from arsenic contaminated well water was also conducted in Taiwan, which determined that a diet with an egg consumption frequency of <1 a week had an odds ratio (OR, an indicator of higher relative risk) of 2.3 relative to those who consume 4 or more eggs, having sweet potato vs. rice as the staple food had an OR of 1.9, meat consumption<1 a week vs. 4 or more had an OR of 1.57, and consuming vegetables<7 days/week vs 7 or more had an OR of 1.43 (ARTSC8:452. The applicant notes that rice has a cyst(e)ine content of 107 mg/100 g (cooked, but dry), while sweet potato has only 14 mg/100 g (QP141.N48:249) and that these risk factors are consistent with there being a correlation between low sulfur amino acid consumption and arsenic toxicity.

6.4.4.3 "Good" Nourishment Doesn't Protect in Northern Chile

Another study investigated whether a well fed population that had been exposed to arsenic in water for centuries had developed a tolerance (EHP108:617). The Atacameno people in Northern Chile are a group that have been drinking arsenic contaminated water for thousands of years. The residents of a small village called Chiu Chiu are a well nourished group whose main economic activity is growing fruits and vegetables, especially carrots. Surprisingly, their prevalence of arsenicosis was found to be at least as great as that of other comparably exposed groups (e.g. in India or Taiwan). The authors of this report note that each of the families that were affected with arsenicosis consumed carrots every day (presumably because they were carrot farmers), but interpreted this as being part of their good nutrition. The applicant notes that carotenoids are known (but apparently not well known) to damage thiols and therefore could be contributing to cysteine deficiency in these otherwise well nourished people, which could explain their heightened sensitivity to arsenic exposure relative to the other families in the village.

The applicant notes that the naturally acquired tolerance (e.g. up regulation of detoxification enzymes) requires dietary cyst(e)ine to be effective, and in the absence of sufficient cyst(e)ine (or in the presence of thiol depletion, such as that produced by carotenoids) the "tolerance" could actually increase the toxicity of arsenic exposure.

6.4.5 Arsenicosis in Peripheral Tissues may be due to Protection of the Internal Organs The applicant has discovered that the amount of cyst(e)ine that is available for the peripheral tissues can be significantly lowered due to competition with the organs and tissues that are served first by the blood stream. The up-regulation of enzymes associated with chronic arsenic exposure increases the cellular uptake of cyst(e)ine for glutathione synthesis in the gut, liver kidney, and presumably other organs and tissues that are well supplied with blood (e.g. the heart) which, especially in the case of deficiency, lowers the availability of cyst(e)ine in the rest of the body. This provides an explanation of why the toxicity of arsenicosis develops sooner and is most prevalent in peripheral tissues such as the skin, hands, and feet.

The digestive tract uses a mucous layer to protect its tissue from proteolytic enzymes, acidity, and toxic substances. The mucous contains glutathione as a protective substance. This glutathione has been found to bind to the consumed arsenic, depleting the glutathione in the process. In response, the de novo synthesis of glutathione in the mucosal cell becomes up-regulated, resulting in twice the normal concentration of glutathione within 3 hours (BBA628:241). The applicant notes that although this is clearly beneficial to the digestive tract, and nominally to the animal as a whole (because it speeds-up the elimination of the arsenic), the cyst(e)ine that is utilized for this depletes the cyst(e)ine that is available for the rest of the body. This cyst(e)ine loss is probably insignificant for a well nourished person, but it becomes significant if the body is already cyst(e)ine deficient.

Further research has indicated that the up-regulated synthesis of glutathione within DiMethyl Arsenic acid (DMA) in cultured Chinese hamster V79 cell has the side effect of decreasing the rate of protein synthesis in these cells (to 70-80% of controls) due to competition for the available cyst(e)ine (ATOX71:730). The applicant notes that this is another indication of how the increased production of glutathione decreases the amount of cyst(e)ine available for other functions and, in effect, increases the dietary requirement of cyst(e)ine for arsenic exposed populations.

Chronic exposure to arsenicals increased GST activity and glutathione levels in rat liver cells (TOXSCI91:70). Interestingly, the liver glutathione level of protein deficient rats has been shown to increase even more than for the well nourished rats (ENVTP8:227). The lever glutathione level in the well fed rats (18% protein in the diet) increased from 88 micrograms per gram to 123, while for the protein deficient (6%) rats it increased from 74 to 134, compared to the controls (which were not exposed to sodium arsenate). The effect on the kidney was less dramatic, but exposure to arsenic did increase the glutathione levels, and the increase was greater for the rats given the low protein diet. The applicant notes that the increase in glutathione in these organs could contribute to glutathione depletion elsewhere in the body for poorly nourished people.

6.4.6 Therapeutic Mitigation of Arsenicosis

The applicant has developed various nutraceutical and dietary supplements that metabolize to thiol and disulfide compounds (such as allyl mercaptan and diallyl disulfide) when consumed by a host. These formulations are taught in detail in the co-pending patent application US2005/0260250A1, which is included by reference. The applicant has now discovered that these can be utilized to augment the bioavailability cysteine to cells including the peripheral tissues of the body, which can in turn augment the glutathione content of these cells. Because many of the symptoms of arsenicosis are caused by (or at least are related to) glutathione depletion, this can be expected to improve the condition of the arsenic-exposed host.

The recommended dosage is 6 "Protein Bound Allyl Mercaptan" capsules per day, typically taken as two capsules with each meal. Each capsule contains 10 mg of AllylSH for a total daily dosage of 60 mg.

7. CLINICAL TRIALS IN BANGLADESH

The applicant had the good fortune to meet Kader Abdul, a PhD student from Bangladesh, when attending the 2005 annual meeting of the International Union of Microbiological Societies in San Francisco. While in Bangladesh, and also later as a PhD student in Stockholm Sweden, Kader had conducted research into the prevention and treatment of arsenicosis and had authored a report on the lack of commercially available technology that is suitable for the removal of arsenic from drinking water. Over the next few months, a plan was developed to conduct a limited-scale clinical trial of the effectiveness of the skin lotion for the treatment of arsenicosis. The goal was to demonstrate proof of feasibility sufficiently to convince a Non-Governmental Organization (NGO) to conduct (and fund) a more comprehensive clinical trial.

Because the costs of the trial would be paid for by the applicant, a budget of $1000 a month was established and multiple phases with associated progress milestones were planned. The project was staffed accordingly with a full time coordinator (Mir Zakir Hassan) located at one of the villages (and traveling to the other villages frequently) and the part-time services of a medical doctor (Dr. Abdus Salam, located in Dhaka) who visits the villages periodically to monitor the patients and is available on-call as necessary. Additional part-time assistance is provided by Pulin Bahari Das (who operates a micro-credit NGO nearby and is well respected by the community). He has set up an awareness program and conducted meetings with the local people.

To provide enough patients, three villages in the Hazigonj district under the Chandpur division in Bangladesh were selected. A questionnaire and informed consent document was used to survey each potential patient, with questions about their socioeconomic conditions, disease symptoms, the tenure of their disease, other associated problems, and which types of medications they use. The patients were taken randomly with the main criteria being that they have visible symptoms of arsenic induced problems on their body.

Initial trials were conducted using three formulations (hereinafter referred to as "skin lotions") that include diallyl disulfide (DADS) as the active ingredient. A control group (using a formulation that omitted the active ingredient) had no significant change in symptoms during a two month initial trial period. The patients using the skin lotions with the active ingredient experienced a significant improvement in symptoms. For example, for the patients using the "ointment" formulation, the symptom of skin roughness was improved 40-60%, the symptom of black spots was improved 30-40%, and the symptom of skin itching was improved 70-100%. These initial trials and the detailed results are described more completely in the co-pending application "Personal Care and Medicinal Products Incorporating Bound Organosulfur Groups" (US2006/0269488A1) by the present applicant.

The next phase of clinical trials involved the administration of dietary supplement capsules that incorporate protein bound allyl mercaptan. The formulation and manufacture of these is described in more detail in the co-pending patent application US2005/0260250A1 by the present applicant.

Ten patients were recruited (8 female and 2 male), with the following age distribution:

15-24 years: 1

25-34 years: 5

35-44 years: 2

45-54 years: 2

The patients exhibited multiple symptoms to varying degrees, with 90% of the patients exhibiting both melanosis and keratosis, 70% exhibiting skin roughness, 40% exhibiting skin cracks, and 20% exhibiting skin ulceration. The patients also suffered from skin itching to varying degrees.

The recommended dosage was 6 "Protein Bound Allyl Mercaptan" capsules per day, typically taken as two capsules with each meal. Each capsule contains 10 mg of AllylSH for a total daily dosage of 60 mg. Several of the patients elected to take only one capsule with each meal (these patients tended to show less improvement than the patients who took both capsules).

The symptoms were significantly improved for all of the patients, as reported by Dr. Abdus Salam. The melanosis improvement was in the range of 35% to 50%. The keratosis improvement was in the range of 20% to 50%. The skin roughness improvement was in the range of 50% to 80%. Most of the patients with skin cracks had significant improvement, with 30% to 80% of the skin cracks disappearing. The skin ulceration improvement was 100%. The patients also described a reduction in skin itching of approximately 50%.

These results are significant, but they are not as dramatic as the improvements that are being obtained from treatment with the skin ointment, who have been using the ointment for over a year now and have seen an improvement in (for example) melanosis averaging 75%. This is probably because most of the symptoms of early stage arcenicosis are skin related, and the ointment can work "from the outside in" while the capsules must work "from the inside out". For the purpose of this study, it was useful to use the ointment and the capsules separately, but it is expected that the best method of treatment will be to use them both together.

Of course, the ideal solution to the arsenic poisoning in India and Bangladesh is to stop drinking the arsenic contaminated water, but the issue of treating the patients still remains. Our next goal is to attract the interest of a large NGO (e.g. the Bangladesh Rural Advancement Committee) in order to be able to conduct a larger scale clinical trial.

The applicant notes that the protein bound allyl mercaptan capsules contain whey protein and therefore each capsule contained approximately 10 mg of cyst(e)ine. Even at the six capsule dosage, this is a small amount compared to the approximately 900 mg of cyst(e)ine in daily dietary protein. However, the excretion of arsenic causes loss of cyst(e)ine and therefore the patients may be somewhat cyst(e)ine depleted even if they are otherwise well nourished. The benefits from the capsules clearly exceed the benefits that would be expected from the small amount of protein that they contain, although the protein content of the capsules is viewed by the applicant as being a beneficial side effect of their formulation. In any case, the active ingredient (AllylSH) was previously shown to be effective in the skin lotion tests. In a future, more extensive, clinical trial in may be useful to include a control group that only consumes the protein component of the capsules.

8. FURTHER EXAMPLES

There are a wide variety of diseases or conditions associated with cysteine depletion, several of which are described herein. Note that this is worded here (and in the claims) as "cysteine depletion", not "cystine depletion" or "cyst(e)ine depletion". The applicant has attempted to rigorously distinguish between these terms throughout the specification, because the distinction is significant to the invention at hand. Although this should be clear throughout the specification, it will be further emphasized and here elaborated upon just to make sure that the point is clear.

The key point is that some biological processes specifically require extracellular cysteine (the thiol). Some published art methods for augmenting the extracellular cysteine (e.g. the administration of N-acetylcysteine) have limited effectiveness because the cysteine that they supply becomes oxidized to cystine and is therefore no longer in the thiol form that is required by these biological processes. To the extent that the accumulation of cystine is toxic, and to the extent that the accumulation of cystine lowers the net cysteine/cystine ratio, these published art methods can be self defeating.

The present invention allows the extracellular concentration of cysteine to be increased at the expense of the cystine concentration, the total cyst(e)ine concentration remaining constant. This is to the benefit of any biological process that requires cysteine, while having neutral benefit to any biological process that depends on cyst(e)ine, and is potentially detrimental to any biological process that requires cystine (although this is typically not an issue due to the relatively high concentration of extracellular cystine in body fluids).

That is not to say that the benefit is limited to the extracellular environment. For example, for the types of cells that can only uptake cysteine, their intracellular cysteine will be depend on the availability of extracellular cysteine. This means that their ability to synthesize glutathione also depends on the availability of extracellular cysteine.

In some cases, this clearly relates to the disease in question. For example, arsenic exposure potentially affects every type of cell in the body. Therefore, those cells that can only uptake cysteine will clearly require the uptake of extracellular cysteine to support their intracellular synthesis of glutathione, which in turn determines their ability to detoxify the arsenic.

As will be seen below, although other researchers have not always distinguished between the effects of extracellular cysteine versus cystine, it is frequently possible to retrospectively attribute an observed benefit (e.g. a benefit from N-acetylcysteine administration) to the augmentation of extracellular cysteine and subsequent biological processes that depend upon it. Typically, this will indicate that the present invention is applicable to the prevention or treatment of the associated disease or condition, and is therefore anticipated as a disease or condition that is covered by the claims.

8.1 The Mitigation of Diabetes

This subject will be primarily addressed by describing the role of cysteine in nonenzymatic transglycation reactions, because this process it little known by most researchers.

8.1.1 Glycation and Transglycation

The enzymatic conjugation of a saccharide (e.g a sugar, such as glucose), to a macromolecule such as a protein is termed glycosylation, and is an important step in the production of macromolecules such as glycoproteins. The corresponding nonenzymatic reaction is termed glycation, and it is frequently related to disease.

Excessive glycation occurs when blood sugar levels are elevated and the presence in the plasma of glycated hemoglobin (e.g. HbA1c) correlates strongly with diabetic complications. Because HbA1c forms slowly and is also removed slowly, it provides a good diagnostic indicator of the average blood sugar level for the previous month or so, and is therefore utilized to monitor the glycemic control of diabetic patients.

The most prevalent initial glycation reaction from high blood sugar is the conjugation between glucose and a lysine residue on a protein, forming a Schiff base. This reaction occurs at a low rate at low blood sugar levels, but is not a problem in this case because it is reversible, which prevents the protein from being permanently damaged. However, the Schiff base can further transform to a much more stable damaged form.

In the case of the glycation of hemoglobin, the time constant for Shiff base formation is a few hours and the concentration of the resulting HbA-aldamine complex reflects the mean glucose level within the past 24 hours (CCA136:75). The second step involves the transformation of the aldamine to a ketoamine which is considerably slower, taking 3-4 weeks to reach a steady state concentration of HbA1c (CCA136:75).

It has recently been discovered that the glycation of proteins occurs at a higher rate than was previously known even at normal blood sugar levels, but this glycation is quickly reversed by thiols such as cysteine (MHPY66:698). The sugar residue is transferred to the thiol and the lysine residue of the protein is completely repaired.

This transfer of the sugar residue from the protein (or other type of macromolecule) to the thiol has been termed "transglycation" and is in some ways analogous to thiol-disulfide exchange reactions. However, cysteine has been shown to be especially effective as a protective transglycation agent because after accepting the sugar residue, it further transforms to a thiazolodine ring structure (variously called G-Cys or Glc-cys in the literature) and therefore becomes unreactive to further exchange reactions. This "traps" the sugar residue and prevents it from participating in further glycation (or transglycation) reactions.

High concentrations of Glc-cys have detected in the urine of diabetic patients (up to 1750 umol/g creatinine) compared to non-diabetic controls (average 10 umol/g creatinine), indicating that transglycation followed by excretion can be an important pathway for protecting proteins during episodes of high blood sugar.

The applicant notes that this implies that the pathology of glycation may actually be result of the loss of repair (e.g. due to cysteine depletion) rather than being directly related to the level of blood sugar itself. The long time constant involved in the formation of stable adducts (such as HbA1c) compared to the relatively high speed of the repair process (e.g the repair of HbA-aldamine by the transglycation with cysteine) further implies a prolonged deficiency, which may be aggravated by the cysteine loss from Glc-cys excretion itself. Therefore, what would otherwise be brief episodes of hyperglycemia can produce a more lasting effect as this cysteine depletion produces a deficiency which persists for a day or more and newly glycated proteins fail to be repaired soon enough to avoid the formation of more permanent damage.

In addition to excretion, other biochemical pathways have been proposed for Glc-cys clearance that only involve relatively unreactive intermediates (ANYAS1043:845).

The applicant notes that at least one of these pathways must be active when glc-cys is being intentionally administered as a prodrug for cysteine (see the section "Cysteine Prodrugs can Increase Glutathione" above).

In any case, bioavailable cysteine has now been shown to be important for the prevention of damage from hyperglycemia, which indicates the benefit of the present invention in the prevention of diabetic complications.

The recommended dosage for the prevention and treatment of diabetes is 6 "Protein Bound Allyl Mercaptan" capsules per day, typically taken as two capsules with each meal.

Other methods to inhibit the formation of glycation products are known. In particular, amino acids which contain an active nitrogen-containing group have been shown to be effective (US005334617A). This method is clearly different from the method of transglycation using thiols (e.g. the method that is augmented by the present invention), yet they both yield similar results (inhibition of the formation of glycation products). The US Patent US005334617A devotes 16 claims to list the diseases that can be treated by this means, all justified within its specification, including complications of diabetes, complications of aging, diabetic kidney disease, glomerulosclerosis, peripheral vascular disease, atherosclerosis, arteriosclerosis, peripheral neuropathy, retinopathy, cataracts, stroke, hypertension, periarticular rigidity, osteoarthritis, loss of elasticity and wrinkling of skin, stiffening of joints, and glomerulonephritis. Rather than repeating the justification for such claims here, the specification of US005334617A is included by reference. Rather than repeating this list of diseases and conditions in the claims, the applicant notes that they all involve the pathology associated with the formation of "super-optimal glycation products" and that those skilled in the art will know that they are therefore suitable for treatment according to the claims of the present invention.

Nearly 10,000 publications on HbA1c have appeared in the literature in the past 30 years (ANYAS1043:9), so perhaps the long list of related disease conditions above should not be a surprise. It is particularly interesting that "HbA1c concentrations predict mortality continuously across the whole population distribution in people without diabetes and at concentrations below those used to diagnose diabetes" (ANYAS1043:9).

8.2 The Mitigation of Cardiovascular Disease

Atherosclerosis accounts for virtually 80% of all deaths among North American diabetes patients, compared with one third of all deaths in the general population (BMCC1:1). These are both incredibly big numbers, and the ability of HbA1c to predict mortality of even non-diabetic people implies that glycation may be a factor involved with cardiovascular disease even in nondiabetic people.

The role of "oxidized LDL" in cardiovascular disease has been well established, especially its role in the development of "foam cells". Oxidized LDL and other forms of chemically modified LDL have been shown to be recognized by the scavenger receptor of macrophages. The oxidized LDL and also the other chemically modified forms of LDL that have this property all tend to have modifications to their lysine groups, which modify the electrostatic charge of the LDL (JBC268:5535). In addition to being taken up by macrophages, chemically modified LDL fails to be degraded in lysosomes and fails to efflux normally, leading to its accumulation inside foam cells (JLR41:1658).

It has already been established that glycation preferentially modifies the lysine residues of proteins. The present application anticipates that this form of chemically modified LDL is a significant factor in the development of cardiovascular disease, and that this is one reason why the HbA1c concentration is a predictor of mortality even in people without diabetes, and that transglycation can be protective.

8.3 Improved Immune Function 8.3.1 Lymphocyte Function

Proper function and immune response of lymphocytes requires a local supply of extracellular cysteine (e.g. from adjacent macrophage cells) because when they are stimulated these cells need to be provided with a higher cysteine concentration than that in circulation (AJM91__3C:140S). However, even when unstimulated, lymphocytes require an adequate supply of cysteine because they lack the ability to uptake cystine. Experiments with mouse spleen lymphocytes have confirmed that lymphocytes are particularly susceptible to intracellular glutathione depletion when they are in a cysteine depleted environment (JCPHY133:330). Cysteine and glutathione dependent lymphocyte functions include the proper expression of NFkB-dependent genes and DNA synthesis (AJM91:3C-140S).

8.3.2 Avoidance of Unnecessary Cell Death

An intense immune response can damage the cells of the host due to the large amount of reactive oxygen species (e.g superoxide, nitric oxide, and peroxynitrite) that are non-specific, damaging microbes and host cells alike. When exposed to reactive oxygen species, the glutathione level within the cell declines, and if it becomes significantly depleted apoptosis can be induced (ECELLB68:47), or even necrotic cell death can occur. Necrotic cell death can cause further damage to the host by provoking an even more intense immune response. Therefore, cells that require the uptake of cysteine (most types of cells) will be more likely to be killed during an intense immune response if cysteine is depleted.

8.3.3 AIDS

Both the cysteine and cystine levels are significantly lowered in HIV-infected patients which is accompanied by an almost complete loss of natural killer cell activity (CCOC-NMC2:227). There is also a decrease in plasma glutamine level that has been shown to be causally related to the Cyst(e)ine deficiency. Together with the increase in plasma glutamine levels, cysteine supplementation (via N-acetylcysteine administration) causes a significant increase in natural killer cell activity and proliferative lymphocyte responses (COCNMC2:227). As discussed elsewhere within this specification, there is potential toxicity associated with dosages of N-acetylcysteine and monitoring of the patient during treatment is recommended.

N-acetylcysteine has been shown be beneficial in the treatment of HIV patients (JMM78:55), but there is a risk of an over-accumulation of cystine due to the oxidation of cysteine (JMMED78:55). A method is therefore needed to allow the cystine level to be significantly increased without also producing an excessive level of cystine. The present invention can be utilized for this because it provides a mechanism for the extracellular cysteine level to be increased at the expense of cystine.

Because HIV-infection lowers both the cysteine and cystine levels it may be desirable for the treatment to increase both the cysteine and cystine levels. In this case, the administration of a combined dosage consisting of both a moderate amount of N-acetylcysteine and protein bound allyl mercaptan would prevent the over-accumulation of cystine that can occur from higher dosages of N-acetylcysteine by continuing to convert the cystine to cysteine. This would allow both the cysteine and cystine levels in the patient to be raised to normal levels simultaneously, without the potential toxicity of excessive cystine accumulation.

8.4 Cancer

Significant loss of body mass occurs during cancer and also from conditions such as AIDS and old age. This primarily involves the loss of skeletal muscle which results in decreased muscle strength and fatigue. This results in a significant loss of quality of life and can limit the patient's willingness to undergo chemotherapy (BLOOD92:59).

The loss of body mass has been shown to be related to the cysteine deficiency that also accompanies these conditions, and it can be significantly reversed by the administration of the cysteine prodrug N-acetylcysteine (BLOOD92:59). Muscle fatigue is also caused by other conditions that cause cysteine depletion such as a high level of activation of the immune system (MHYP53:347). The high level of immune system activation associated with cancer may be one of the causes of cyst(e)ine loss.

The present invention can be used to increase the level of cysteine at the expense of cystine, or it can be utilized in conjunction with a cysteine prodrug if it is desired to raise both the cysteine and cystine levels in the patient.

Interestingly, protein bound allyl mercaptan includes a moderate amount of cyst(e)ine in the protein which can equal or exceed the amount of allyl mercaptan in the dose. In most cases this is only a minor source of cysteine compared to the amount of dietary cystein that is consumed, but in conditions of cyst(e)ine depletion it could be beneficial.

8.5 Physiological Aging

We all age with time, but the rate of physiological aging and the development of age related conditions varies between individuals.

The aging related loss in skeletal muscle and body mass is due to a reduction in the rate of protein synthesis which in turn is due to cysteine starvation. Loss of muscle function is typically associated with compromised physical and social functions, loss of independence, and psychological stress (PTRSB360:2355). Therefore, the mitigation of the cysteine starvation related decline in protein synthesis will also alleviate a variety of aging related conditions.

The aging related decline in extracellular cysteine concentration and the fact that many types of cells can only uptake cysteine (not cystine) have already been described several times within the specification. That the augmentation of extracellular cysteine can improve the nourishment of these cells has also been established.

The present invention has been illustrated primarily according to its application to diseases and conditions that are known to be associated with cysteine depletion, but given the benefit of this disclosure those skilled in the art will realize that it can also be applied to other conditions, such as to raise the cysteine level to a level above that associated with identified deficiency. Therefore, the invention is not limited to the above description and illustrations, but is defined by the appended claims.

What is claimed is:

1. A method of treating a cysteine depletion dependent disease or condition selected from the group consisting of
   (a) the condition of hyperpigmentation associated with the disease of arsenicosis,
   (b) the condition of glycated hemoglobin associated with the disease of diabetes,
   (c) the condition of glycated low density lipoprotein associated with cardiovascular disease,
   (d) the condition of the loss of skeletal muscle associated with the disease of AIDS,
   (e) the condition of the loss of skeletal muscle associated with a disease of cancer,
   (f) the condition of super-optimal glycation products due to an insufficient rate of transglycation,
   (g) the condition of the loss of skeletal muscle due to physiological aging, or
   (h) the condition of muscle fatigue due to a high level of activation of the immune system
   said method comprising:
   administering to an animal in need thereof an effective amount of a composition comprising a membrane permeable thiol in the form of said membrane permeable thiol itself or in the form of said membrane permeable thiol disulfide bonded to protein that metabolizes in vivo to produce said membrane permeable thiol;
   wherein said membrane permeable thiol reduces extracellular cystine or a mixed cysteine disulfide to produce extracellular cysteine and is concurrently oxidized to a disulfide or mixed disulfide;
   wherein said disulfide or mixed disulfide is membrane permeable or forms a membrane permeable disulfide or membrane permeable mixed disulfide, which upon cell entry is reduced and re-forms said membrane permeable thiol.

2. The method of claim 1, wherein said administering of said composition produces an increase in the bioavailability of cysteine in said animal.

3. The method of claim 2, wherein said administering of said composition produces an increase in the ratio of plasma cysteine to cystine in said animal.

4. The method of claim 2, wherein said administering of said composition produces an increase in the amount of intracellular glutathione in said animal.

5. The method of claim 1, wherein said administering of said composition produces an increase in the level of plasma albumin in said animal.

6. The method of claim 1, 2, 3, 4, or 5 wherein said membrane permeable thiol is allyl mercaptan or propyl mercaptan in an effective amount up to 5,000 mg per daily dosage.

7. The method of claim 6 wherein said membrane permeable thiol is administered in the form of a mixed disulfide with protein in a dosage sufficient for the composition to metabolize to said membrane permeable thiol in an effective amount up to 250 mg per daily dosage.

8. The method of claim 7 wherein said composition is a nutraceutical.

9. The method of claim 7 wherein said composition is a dietary supplement.

10. The method of claim 6 wherein said composition is a drug.

11. The method of claim 1, 2, 3, 4, or 5 wherein said animal is a human.

12. The method of claim 1, wherein said animal is afflicted by the disease of arsenicosis and said condition is hyperpigmentation.

13. The method of claim 1, wherein said animal is afflicted by the disease of diabetes and said condition is glycated hemoglobin.

14. The method of claim 1, wherein said animal is afflicted by cardiovascular disease and said condition is glycated low density lipoprotein.

15. The method of claim 1, wherein said animal is afflicted by the disease of AIDS and said condition is the loss of skeletal muscle.

16. The method of claim 1, wherein said animal is afflicted by the disease of cancer and said condition is the loss of skeletal muscle.

17. The method of claim 1, wherein said animal is afflicted with the condition of super-optimal glycation products due to an insufficient rate of transglycation.

18. The method of claim 1, wherein said animal is afflicted by physiological aging and said condition is loss of skeletal muscle.

19. The method of claim 1, wherein said animal is afflicted with the condition of muscle fatigue due to a high level of activation of the immune system.

* * * * *